(12) United States Patent
Dong et al.

US007531621B1

(10) Patent No.: US 7,531,621 B1
(45) Date of Patent: May 12, 2009

(54) PTH2 RECEPTOR SELECTIVE COMPOUNDS

(75) Inventors: Zheng Xin Dong, Framingham, MA (US); Michael Chorev, Chestnut Hill, MA (US); Michael Rosenblatt, Newton Centre, MA (US)

(73) Assignees: Societe de Conseils de Recherches et d'Applications Scientifiques S.A.S., Paris (FR); Beth Israel, Boston, MA (US)

( * ) Notice: Subject to any disclaimer, the term of this patent is extended or adjusted under 35 U.S.C. 154(b) by 0 days.

(21) Appl. No.: 09/674,597

(22) PCT Filed: May 3, 1999

(86) PCT No.: PCT/US99/09521

§ 371 (c)(1),
(2), (4) Date: Apr. 9, 2001

(87) PCT Pub. No.: WO99/57139

PCT Pub. Date: Nov. 11, 1999

(51) Int. Cl.
*C07K 5/00* (2006.01)
*A61K 38/16* (2006.01)
*A61K 38/29* (2006.01)
*A61K 38/00* (2006.01)

(52) U.S. Cl. .......................... 530/300; 530/324; 514/2; 514/12

(58) Field of Classification Search ................. 530/300, 530/350, 402, 399, 351; 514/12
See application file for complete search history.

(56) References Cited

U.S. PATENT DOCUMENTS

| | | | |
|---|---|---|---|
| 4,968,669 A | 11/1990 | Rosenblatt et al. | |
| 5,001,223 A * | 3/1991 | Rosenblatt et al. | .......... 530/324 |
| 5,087,562 A | 2/1992 | Rosenblatt et al. | |
| 5,093,233 A | 3/1992 | Rosenblatt et al. | |
| 5,149,779 A | 9/1992 | Chorev et al. | |
| 5,393,869 A | 2/1995 | Nakagawa et al. | |
| 5,446,130 A | 8/1995 | Kanmera et al. | |
| 5,527,772 A | 6/1996 | Holick | |
| 5,556,940 A * | 9/1996 | Willick et al. | ................ 530/317 |
| 5,589,452 A | 12/1996 | Krstenansky et al. | |
| 5,717,062 A * | 2/1998 | Chorev et al. | ................ 530/317 |
| 5,723,577 A * | 3/1998 | Dong | ........................ 530/324 |
| 5,783,558 A | 7/1998 | Duvos et al. | |
| 5,955,574 A * | 9/1999 | Dong | ........................ 530/324 |
| 5,969,095 A | 10/1999 | Dong | |

FOREIGN PATENT DOCUMENTS

| | | |
|---|---|---|
| EP | 0 293 158 | 11/1988 |
| EP | 0 341 962 | 11/1989 |
| EP | 0 477 885 | 9/1991 |
| GB | 2 269 176 | 2/1994 |
| WO | WO 92/11286 | 7/1992 |
| WO | WO 94/01460 | 1/1994 |
| WO | WO 94/02510 | 2/1994 |
| WO | WO 96/40193 | 12/1996 |
| WO | WO 97/02834 | 1/1997 |
| WO | WO 98/14478 | 4/1998 |
| WO | WO 98/04591 | 2/2005 |

OTHER PUBLICATIONS

Usdin, T., 1995, J. Biol. Chem. 138(2): 831-834.*
Marx, U., 1996, Accession No. 1ZWC, chain 32.*
Weaver, et al, 1993, Accession No. AAA30749.*
Niall, et al, 1992, Accession No. 701028A.*
Usdin, T., 1997, Evidence for a Parathyroid Hormone-2 receptor selective ligand in the hypothalamus. Endocrinology, 138(2): 831-834.*
Wright, et al., 1987, PNAS, 84: 26-30.*
Zhou, et al, 1997, PNAS, 94: 3644-3649.*
Yamamoto, et al, 1997, Endocrinology, 138(5): 2066-2072.*
Usdin, et al, 1995, J. Biol. Chem., 270(26): 15455-15458.*
Gardella, et al, 1996, J. Biol. Chem., 271(33): 19888-19893.*
Chorev, et al, 1990, Biochemistry, 29: 1580-1586.*
Neugebauer and Willick, 1993, "Peptides 1992", C.H. Schneider and A.N. Eberte (eds), ESCOM Science Publishers.*
Usdin, et al, 2003, Emerging functions for tuberoinfundibular peptide of 39 residues. Trends in Endocrinology and Metabolism, 14(1): 14-19.*
Gardella, Thomas J. et al.; "Converting Parathyroid Hormone-Related Peptide (PTHrP) into a Potent PTH-2 Receptor Agonist"; Journal of Biological Chemistry, US, American Society of Biological Chemists, Baltimore, MD,; vol. 271, No. 33 pp. 19888-19893; (1996).
Usdin, Ted B.; "Evidence for a Parathyroid Hormone-2 receptor selective ligand in the hypothalamus" Endocrinology, vol. 138, No. 2, pp. 831-834; (1997).
Behar, V. et al.; "Histidine at Position 5 Is the Specificity "Switch" between Two Parathyroid Hormone Receptor Subtypes"; Endocrinology vol. 137, No. 10; pp. 4217-4224; (1996).
Nakamoto, C. et al., "Probing the Bimolecular Interactions . . . ", Biochemistry, vol. 34, No. 33, pp. 10546-10552 (1995).
Neugebauer, W. et al., "Lactam Analogues of a Human Parathyroid . . . ", Peptides, C. H. Schneider and A. N. Eberle (Eds), Escom Science Publishers B. V., pp. 395-396 (1992).

(Continued)

*Primary Examiner*—Dong Jiang
*Assistant Examiner*—Sandra Wegert
(74) *Attorney, Agent, or Firm*—Fish & Richardson; Alan F. Feeney; Tony K. Uhm

(57) ABSTRACT

This invention relates to a series of PTH and PTHrP analogues that selectively bind to PTH2 receptors and as such may be useful in treating abnormal CNS functions; abnormal pancreatic functions; divergence from normal mineral metabolism and homeostasis; male infertility; regulation of abnormal blood pressure; and hypothalmic disease.

3 Claims, No Drawings

OTHER PUBLICATIONS

Usdin, T. B. et al., "Distribution of Parathyroid Hormone-2 Receptor Messenger Ribonucleic Acid in Rat", Endocrinology, vol. 137, No. 10, pp. 4285-4297 (1996).

Behar, V. et al., "The Human PTH2 Receptor: . . . ", Endocrinology, vol. 137, No. 7, pp. 2748-2757, (1996).

Chorev, M. et al., "Modifications of Position 12 in Parathyroid . . . ", Biochemistry, vol. 29, No. 6, pp. 1580-1586 (1990).

Gombert, F.O. et al., "Alanine and D-Amino Acid Scan of Human . . . ", Peptides: Chemistry, Structure and Biology, Pravin T.P. Kanmaya and Robert S. Hodges (Eds), Mayflower Scientific Ltd., pp. 661-662, (1996).

Clark, J. A. et al., "Multiple Regions of Ligand Discrimination Revealed by Analysis of Chimeric Parathyroid Hormone 2 (PTH3) and PTH/PTH-Related Peptide (PTHrP) Receptors," Molecular Endocrinology, 1998, 12(2):193-206.

Arimura, A. et al., "Pituitary Adenylate Cyclase Activating Polypeptide (PACAP) and its Receptors: Neuroendocrine and Endocrine Interaction," Frontiers in Neuroendocrinology, 1995, 16:53-88.

Arimura, A., "Pituitary Adenylate Cyclase Activating Polypeptide (PACAP): discovery and current status of research," Regulatory Peptides, 1992, 37:287-303.

Christophe, J., "Type I receptors for PACAP (A Neuropeptide even more important that VIP?)," Biochemica et Biophysica Acta, 1993, 1154:183-189.

Clark, J. A. et al., "Analysis of peptide ligand discrimination by the PTH/PTHrP and PTH2 receptors," Abstr. Soc. Neuroscience, 1997, 23:673, #267.7.

\* cited by examiner

SEQUENCE LISTING

```
<160> NUMBER OF SEQ ID NOS: 53

<210> SEQ ID NO 1
<211> LENGTH: 34
<212> TYPE: PRT
<213> ORGANISM: Homo sapiens

<400> SEQUENCE: 1

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 2
<211> LENGTH: 34
<212> TYPE: PRT
<213> ORGANISM: Homo sapiens

<400> SEQUENCE: 2

Ala Val Ser Glu His Gln Leu Leu His Asp Lys Gly Lys Ser Ile Gln
1               5                   10                  15

Asp Leu Arg Arg Arg Phe Phe Leu His His Leu Ile Ala Glu Ile His
            20                  25                  30

Thr Ala

<210> SEQ ID NO 3
<211> LENGTH: 34
<212> TYPE: PRT
<213> ORGANISM: Artificial Sequence
<220> FEATURE:
<223> OTHER INFORMATION: non-naturally occurring polypeptide
<220> FEATURE:
<221> NAME/KEY: AMIDATION
<222> LOCATION: 34

<400> SEQUENCE: 3

Ala Val Ser Glu Ile Gln Leu Leu His Asp Lys Gly Lys Ser Ile Gln
1               5                   10                  15

Asp Leu Arg Arg Arg Phe Phe Leu His His Leu Ile Ala Glu Ile His
            20                  25                  30
```

Thr Ala

```
<210> SEQ ID NO 4
<211> LENGTH: 34
<212> TYPE: PRT
<213> ORGANISM: Artificial Sequence
<220> FEATURE:
<223> OTHER INFORMATION: non-naturally occurring polypeptide
<220> FEATURE:
<221> NAME/KEY: MOD_RES
<222> LOCATION: 34
<223> OTHER INFORMATION: amino acid is attached to R3, which represents
      OH, NH2, (C1-C30)alkoxy or NH-Y-CH2-Z, where Y is a
      (C1-C30) hydrocarbon moiety and Z is CO2H or CONH2

<400> SEQUENCE: 4

Ser Val Ser Glu Ile Gln Leu Met His Asn Leu Gly Lys His Leu Asn
 1               5                  10                  15

Ser Met Glu Arg Val Glu Trp Leu Arg Lys Lys Leu Gln Asp Val His
                20                  25                  30

Asn Phe

<210> SEQ ID NO 5
<211> LENGTH: 35
<212> TYPE: PRT
<213> ORGANISM: Artificial Sequence
<220> FEATURE:
<223> OTHER INFORMATION: non-naturally occurring polypeptide
<220> FEATURE:
<221> NAME/KEY: MOD_RES
<222> LOCATION: 35
<223> OTHER INFORMATION: amino acid is attached to R3, which represents
      OH, NH2, (C1-C30)alkoxy or NH-Y-CH2-Z, where Y is a
      (C1-C30) hydrocarbon moiety and Z is CO2H or CONH2

<400> SEQUENCE: 5

Ser Val Ser Glu Ile Gln Leu Met His Asn Leu Gly Lys His Leu Asn
 1               5                  10                  15

Ser Met Glu Arg Val Glu Trp Leu Arg Lys Lys Leu Gln Asp Val His
                20                  25                  30

Asn Phe Val
        35

<210> SEQ ID NO 6
<211> LENGTH: 36
<212> TYPE: PRT
<213> ORGANISM: Artificial Sequence
<220> FEATURE:
<223> OTHER INFORMATION: non-naturally occurring polypeptide
<220> FEATURE:
<221> NAME/KEY: MOD_RES
<222> LOCATION: 36
<223> OTHER INFORMATION: amino acid is attached to R3, which represents
      OH, NH2, (C1-C30)alkoxy or NH-Y-CH2-Z, where Y is a
      (C1-C30) hydrocarbon moiety and Z is CO2H or CONH2

<400> SEQUENCE: 6

Ser Val Ser Glu Ile Gln Leu Met His Asn Leu Gly Lys His Leu Asn
 1               5                  10                  15

Ser Met Glu Arg Val Glu Trp Leu Arg Lys Lys Leu Gln Asp Val His
                20                  25                  30

Asn Phe Val Ala
        35

<210> SEQ ID NO 7
<211> LENGTH: 37
```

```
<212> TYPE: PRT
<213> ORGANISM: Artificial Sequence
<220> FEATURE:
<223> OTHER INFORMATION: non-naturally occurring polypeptide
<220> FEATURE:
<221> NAME/KEY: MOD_RES
<222> LOCATION: 37
<223> OTHER INFORMATION: amino acid is attached to R3, which represents
      OH, NH2, (C1-C30)alkoxy or NH-Y-CH2-Z, where Y is a
      (C1-C30) hydrocarbon moiety and Z is CO2H or CONH2

<400> SEQUENCE: 7

Ser Val Ser Glu Ile Gln Leu Met His Asn Leu Gly Lys His Leu Asn
 1               5                  10                  15

Ser Met Glu Arg Val Glu Trp Leu Arg Lys Lys Leu Gln Asp Val His
                20                  25                  30

Asn Phe Val Ala Leu
            35

<210> SEQ ID NO 8
<211> LENGTH: 38
<212> TYPE: PRT
<213> ORGANISM: Artificial Sequence
<220> FEATURE:
<223> OTHER INFORMATION: non-naturally occurring polypeptide
<220> FEATURE:
<221> NAME/KEY: MOD_RES
<222> LOCATION: 38
<223> OTHER INFORMATION: amino acid is attached to R3, which represents
      OH, NH2, (C1-C30)alkoxy or NH-Y-CH2-Z, where Y is a
      (C1-C30) hydrocarbon moiety and Z is CO2H or CONH2

<400> SEQUENCE: 8

Ser Val Ser Glu Ile Gln Leu Met His Asn Leu Gly Lys His Leu Asn
 1               5                  10                  15

Ser Met Glu Arg Val Glu Trp Leu Arg Lys Lys Leu Gln Asp Val His
                20                  25                  30

Asn Phe Val Ala Leu Gly
            35

<210> SEQ ID NO 9
<211> LENGTH: 34
<212> TYPE: PRT
<213> ORGANISM: Artificial Sequence
<220> FEATURE:
<223> OTHER INFORMATION: non-naturally occurring polypeptide
<220> FEATURE:
<221> NAME/KEY: MOD_RES
<222> LOCATION: 34
<223> OTHER INFORMATION: amino acid is attached to R3, which represents
      OH, NH2, (C1-C30)alkoxy or NH-Y-CH2-Z, where Y is a
      (C1-C30) hydrocarbon moiety and Z is CO2H or CONH2

<400> SEQUENCE: 9

Ala Val Ser Glu His Gln Leu Leu His Asp Lys Gly Lys Ser Ile Gln
 1               5                  10                  15

Asp Leu Arg Arg Arg Phe Phe Leu His His Leu Ile Ala Glu Ile His
                20                  25                  30

Thr Ala

<210> SEQ ID NO 10
<211> LENGTH: 35
<212> TYPE: PRT
<213> ORGANISM: Artificial Sequence
<220> FEATURE:
<223> OTHER INFORMATION: non-naturally occurring polypeptide
<220> FEATURE:
```

```
<221> NAME/KEY: MOD_RES
<222> LOCATION: 35
<223> OTHER INFORMATION: amino acid is attached to R3, which represents
      OH, NH2, (C1-C30)alkoxy or NH-Y-CH2-Z, where Y is a
      (C1-C30) hydrocarbon moiety and Z is CO2H or CONH2

<400> SEQUENCE: 10

Ala Val Ser Glu His Gln Leu Leu His Asp Lys Gly Lys Ser Ile Gln
 1               5                  10                  15

Asp Leu Arg Arg Arg Phe Phe Leu His Leu Ile Ala Glu Ile His
            20                  25                  30

Thr Ala Glu
        35

<210> SEQ ID NO 11
<211> LENGTH: 36
<212> TYPE: PRT
<213> ORGANISM: Artificial Sequence
<220> FEATURE:
<223> OTHER INFORMATION: non-naturally occurring polypeptide
<220> FEATURE:
<221> NAME/KEY: MOD_RES
<222> LOCATION: 36
<223> OTHER INFORMATION: amino acid is attached to R3, which represents
      OH, NH2, (C1-C30)alkoxy or NH-Y-CH2-Z, where Y is a
      (C1-C30) hydrocarbon moiety and Z is CO2H or CONH2

<400> SEQUENCE: 11

Ala Val Ser Glu His Gln Leu Leu His Asp Lys Gly Lys Ser Ile Gln
 1               5                  10                  15

Asp Leu Arg Arg Arg Phe Phe Leu His Leu Ile Ala Glu Ile His
            20                  25                  30

Thr Ala Glu Ile
        35

<210> SEQ ID NO 12
<211> LENGTH: 37
<212> TYPE: PRT
<213> ORGANISM: Artificial Sequence
<220> FEATURE:
<223> OTHER INFORMATION: non-naturally occurring polypeptide
<220> FEATURE:
<221> NAME/KEY: MOD_RES
<222> LOCATION: 37
<223> OTHER INFORMATION: amino acid is attached to R3, which represents
      OH, NH2, (C1-C30)alkoxy or NH-Y-CH2-Z, where Y is a
      (C1-C30) hydrocarbon moiety and Z is CO2H or CONH2

<400> SEQUENCE: 12

Ala Val Ser Glu His Gln Leu Leu His Asp Lys Gly Lys Ser Ile Gln
 1               5                  10                  15

Asp Leu Arg Arg Arg Phe Phe Leu His Leu Ile Ala Glu Ile His
            20                  25                  30

Thr Ala Glu Ile Arg
        35

<210> SEQ ID NO 13
<211> LENGTH: 38
<212> TYPE: PRT
<213> ORGANISM: Artificial Sequence
<220> FEATURE:
<223> OTHER INFORMATION: non-naturally occurring polypeptide
<220> FEATURE:
<221> NAME/KEY: MOD_RES
<222> LOCATION: 38
<223> OTHER INFORMATION: amino acid is attached to R3, which represents
      OH, NH2, (C1-C30)alkoxy or NH-Y-CH2-Z, where Y is a
```

(C1-C30) hydrocarbon moiety and Z is CO2H or CONH2

<400> SEQUENCE: 13

Ala Val Ser Glu His Gln Leu Leu His Asp Lys Gly Lys Ser Ile Gln
 1               5                  10                  15

Asp Leu Arg Arg Arg Phe Phe Leu His His Leu Ile Ala Glu Ile His
                20                  25                  30

Thr Ala Glu Ile Arg Ala
            35

<210> SEQ ID NO 14
<211> LENGTH: 36
<212> TYPE: PRT
<213> ORGANISM: Artificial Sequence
<220> FEATURE:
<223> OTHER INFORMATION: non-naturally occurring polypeptide

<400> SEQUENCE: 14

Ala Val Ser Glu Ile Gln Leu Leu His Asp Lys Gly Lys Ser Ile Gln
 1               5                  10                  15

Asp Leu Arg Arg Arg Phe Trp Leu His His Leu Ile Ala Glu Ile His
                20                  25                  30

Thr Ala Glu Ile
            35

<210> SEQ ID NO 15
<211> LENGTH: 36
<212> TYPE: PRT
<213> ORGANISM: Artificial Sequence
<220> FEATURE:
<223> OTHER INFORMATION: non-naturally occurring polypeptide

<400> SEQUENCE: 15

Ala Val Ser Glu His Gln Leu Leu His Asp Lys Gly Lys Ser Ile Gln
 1               5                  10                  15

Asp Leu Arg Arg Arg Phe Trp Leu His His Leu Ile Ala Glu Ile His
                20                  25                  30

Thr Ala Glu Ile
            35

<210> SEQ ID NO 16
<211> LENGTH: 33
<212> TYPE: PRT
<213> ORGANISM: Artificial Sequence
<220> FEATURE:
<223> OTHER INFORMATION: non-naturally occurring polypeptide
<220> FEATURE:
<221> NAME/KEY: MOD_RES
<222> LOCATION: 7, 10
<223> OTHER INFORMATION: Xaa = cyclohexylalanine (Cha)
<220> FEATURE:
<221> NAME/KEY: MOD_RES
<222> LOCATION: 17
<223> OTHER INFORMATION: Xaa = norleucine (Nle)
<220> FEATURE:
<221> NAME/KEY: AMIDATION
<222> LOCATION: 33

<400> SEQUENCE: 16

Ser Val Ser Glu Ile Gln Xaa His Asn Xaa Gly Lys His Leu Asn Ser
 1               5                  10                  15

Xaa Glu Arg Val Glu Trp Leu Arg Lys Lys Leu Gln Asp Val His Asn
                20                  25                  30

Tyr

```
<210> SEQ ID NO 17
<211> LENGTH: 34
<212> TYPE: PRT
<213> ORGANISM: Artificial Sequence
<220> FEATURE:
<223> OTHER INFORMATION: non-naturally occurring polypeptide
<220> FEATURE:
<221> NAME/KEY: MOD_RES
<222> LOCATION: 8, 18
<223> OTHER INFORMATION: Xaa = norleucine (Nle)
<220> FEATURE:
<221> NAME/KEY: MOD_RES
<222> LOCATION: 34
<223> OTHER INFORMATION: Xaa = [125I]-3-iodotyrosine
<220> FEATURE:
<221> NAME/KEY: AMIDATION
<222> LOCATION: 34

<400> SEQUENCE: 17

Ala Val Ser Glu Ile Gln Phe Xaa His Asn Leu Gly Lys His Leu Ser
 1               5                  10                  15

Ser Xaa Glu Arg Val Glu Trp Leu Arg Lys Lys Leu Gln Asp Val His
            20                  25                  30

Asn Xaa

<210> SEQ ID NO 18
<211> LENGTH: 33
<212> TYPE: PRT
<213> ORGANISM: Artificial Sequence
<220> FEATURE:
<223> OTHER INFORMATION: non-naturally occurring polypeptide
<220> FEATURE:
<221> NAME/KEY: AMIDATION
<222> LOCATION: 33

<400> SEQUENCE: 18

Ser Val Ser Glu Ile Gln Leu His Asn Leu Gly Lys His Leu Asn Ser
 1               5                  10                  15

Met Glu Arg Val Glu Trp Leu Arg Lys Lys Leu Gln Asp Val His Asn
            20                  25                  30

Phe

<210> SEQ ID NO 19
<211> LENGTH: 33
<212> TYPE: PRT
<213> ORGANISM: Artificial Sequence
<220> FEATURE:
<223> OTHER INFORMATION: non-naturally occurring polypeptide
<220> FEATURE:
<221> NAME/KEY: MOD_RES
<222> LOCATION: 7, 10
<223> OTHER INFORMATION: Xaa = cyclohexylalanine (Cha)
<220> FEATURE:
<221> NAME/KEY: AMIDATION
<222> LOCATION: 33

<400> SEQUENCE: 19

Ser Val Ser Glu Ile Gln Xaa His Asn Xaa Gly Lys His Leu Asn Ser
 1               5                  10                  15

Met Glu Arg Val Glu Trp Leu Arg Lys Lys Leu Gln Asp Val His Asn
            20                  25                  30

Phe

<210> SEQ ID NO 20
<211> LENGTH: 32
```

```
<212> TYPE: PRT
<213> ORGANISM: Artificial Sequence
<220> FEATURE:
<223> OTHER INFORMATION: non-naturally occurring polypeptide
<220> FEATURE:
<221> NAME/KEY: MOD_RES
<222> LOCATION: 7, 10
<223> OTHER INFORMATION: Xaa = cyclohexylalanine (Cha)
<220> FEATURE:
<221> NAME/KEY: AMIDATION
<222> LOCATION: 32

<400> SEQUENCE: 20

Ser Val Ser Glu Ile Gln Xaa His Asn Xaa Gly Lys His Leu Asn Ser
 1               5                  10                  15

Glu Arg Val Glu Trp Leu Arg Lys Lys Leu Gln Asp Val His Asn Tyr
            20                  25                  30

<210> SEQ ID NO 21
<211> LENGTH: 32
<212> TYPE: PRT
<213> ORGANISM: Artificial Sequence
<220> FEATURE:
<223> OTHER INFORMATION: non-naturally occurring polypeptide
<220> FEATURE:
<221> NAME/KEY: AMIDATION
<222> LOCATION: 32

<400> SEQUENCE: 21

Ser Val Ser Glu Ile Gln Leu His Asn Leu Gly Lys His Leu Asn Ser
 1               5                  10                  15

Glu Arg Val Glu Trp Leu Arg Lys Lys Leu Gln Asp Val His Asn Phe
            20                  25                  30

<210> SEQ ID NO 22
<211> LENGTH: 32
<212> TYPE: PRT
<213> ORGANISM: Artificial Sequence
<220> FEATURE:
<223> OTHER INFORMATION: non-naturally occurring polypeptide
<220> FEATURE:
<221> NAME/KEY: MOD_RES
<222> LOCATION: 7, 10
<223> OTHER INFORMATION: Xaa = cyclohexylalanine (Cha)
<220> FEATURE:
<221> NAME/KEY: AMIDATION
<222> LOCATION: 32

<400> SEQUENCE: 22

Ser Val Ser Glu Ile Gln Xaa His Asn Xaa Gly Lys His Leu Asn Ser
 1               5                  10                  15

Glu Arg Val Glu Trp Leu Arg Lys Lys Leu Gln Asp Val His Asn Phe
            20                  25                  30

<210> SEQ ID NO 23
<211> LENGTH: 33
<212> TYPE: PRT
<213> ORGANISM: Artificial Sequence
<220> FEATURE:
<223> OTHER INFORMATION: non-naturally occurring polypeptide
<220> FEATURE:
<221> NAME/KEY: MOD_RES
<222> LOCATION: 17
<223> OTHER INFORMATION: Xaa = norleucine (Nle)
<220> FEATURE:
<221> NAME/KEY: AMIDATION
<222> LOCATION: 33

<400> SEQUENCE: 23
```

```
Ser Val Ser Glu Ile Gln Leu His Asn Leu Gly Lys His Leu Asn Ser
 1               5                  10                  15

Xaa Glu Arg Val Glu Trp Leu Arg Lys Lys Leu Gln Asp Val His Asn
            20                  25                  30

Tyr
```

<210> SEQ ID NO 24
<211> LENGTH: 33
<212> TYPE: PRT
<213> ORGANISM: Artificial Sequence
<220> FEATURE:
<223> OTHER INFORMATION: non-naturally occurring polypeptide
<220> FEATURE:
<221> NAME/KEY: AMIDATION
<222> LOCATION: 33

<400> SEQUENCE: 24

```
Ser Val Ser Glu Ile Gln Leu Met His Asn Leu Gly Lys His Leu Asn
 1               5                  10                  15

Ser Glu Arg Val Glu Trp Leu Arg Lys Lys Leu Gln Asp Val His Asn
            20                  25                  30

Phe
```

<210> SEQ ID NO 25
<211> LENGTH: 33
<212> TYPE: PRT
<213> ORGANISM: Artificial Sequence
<220> FEATURE:
<223> OTHER INFORMATION: non-naturally occurring polypeptide
<220> FEATURE:
<221> NAME/KEY: MOD_RES
<222> LOCATION: 7, 11
<223> OTHER INFORMATION: Xaa = cyclohexylalanine (Cha)
<220> FEATURE:
<221> NAME/KEY: AMIDATION
<222> LOCATION: 33

<400> SEQUENCE: 25

```
Ser Val Ser Glu Ile Gln Xaa Met His Asn Xaa Gly Lys His Leu Asn
 1               5                  10                  15

Ser Glu Arg Val Glu Trp Leu Arg Lys Lys Leu Gln Asp Val His Asn
            20                  25                  30

Phe
```

<210> SEQ ID NO 26
<211> LENGTH: 33
<212> TYPE: PRT
<213> ORGANISM: Artificial Sequence
<220> FEATURE:
<223> OTHER INFORMATION: non-naturally occurring polypeptide
<220> FEATURE:
<221> NAME/KEY: MOD_RES
<222> LOCATION: 7, 11
<223> OTHER INFORMATION: Xaa = cyclohexylalanine (Cha)
<220> FEATURE:
<221> NAME/KEY: AMIDATION
<222> LOCATION: 33

<400> SEQUENCE: 26

```
Ser Val Ser Glu Ile Gln Xaa Met His Asn Xaa Gly Lys His Leu Asn
 1               5                  10                  15

Ser Glu Arg Val Glu Trp Leu Arg Lys Lys Leu Gln Asp Val His Asn
            20                  25                  30

Tyr
```

```
<210> SEQ ID NO 27
<211> LENGTH: 33
<212> TYPE: PRT
<213> ORGANISM: Artificial Sequence
<220> FEATURE:
<223> OTHER INFORMATION: non-naturally occurring polypeptide
<220> FEATURE:
<221> NAME/KEY: MOD_RES
<222> LOCATION: 7, 17
<223> OTHER INFORMATION: Xaa = norleucine (Nle)
<220> FEATURE:
<221> NAME/KEY: AMIDATION
<222> LOCATION: 33

<400> SEQUENCE: 27

Ser Val Ser Glu Ile Leu Xaa His Asn Leu Gly Lys His Leu Asn Ser
 1               5                  10                  15

Xaa Glu Arg Val Glu Trp Leu Arg Lys Lys Leu Gln Asp Val His Asn
                20                  25                  30

Tyr

<210> SEQ ID NO 28
<211> LENGTH: 33
<212> TYPE: PRT
<213> ORGANISM: Artificial Sequence
<220> FEATURE:
<223> OTHER INFORMATION: non-naturally occurring polypeptide
<220> FEATURE:
<221> NAME/KEY: MOD_RES
<222> LOCATION: 7, 17
<223> OTHER INFORMATION: Xaa = norleucine (Nle)
<220> FEATURE:
<221> NAME/KEY: AMIDATION
<222> LOCATION: 33

<400> SEQUENCE: 28

Ser Val Ser Glu Ile Gln Xaa His Asn Leu Gly Lys His Leu Asn Ser
 1               5                  10                  15

Xaa Glu Arg Val Glu Trp Leu Arg Lys Lys Leu Gln Asp Val His Asn
                20                  25                  30

Tyr

<210> SEQ ID NO 29
<211> LENGTH: 33
<212> TYPE: PRT
<213> ORGANISM: Artificial Sequence
<220> FEATURE:
<223> OTHER INFORMATION: non-naturally occurring polypeptide
<220> FEATURE:
<221> NAME/KEY: MOD_RES
<222> LOCATION: 8, 17
<223> OTHER INFORMATION: Xaa = norleucine (Nle)
<220> FEATURE:
<221> NAME/KEY: AMIDATION
<222> LOCATION: 33

<400> SEQUENCE: 29

Ser Val Ser Glu Ile Gln Leu Xaa Asn Leu Gly Lys His Leu Asn Ser
 1               5                  10                  15

Xaa Glu Arg Val Glu Trp Leu Arg Lys Lys Leu Gln Asp Val His Asn
                20                  25                  30

Tyr

<210> SEQ ID NO 30
<211> LENGTH: 33
<212> TYPE: PRT
```

<213> ORGANISM: Artificial Sequence
<220> FEATURE:
<223> OTHER INFORMATION: non-naturally occurring polypeptide
<220> FEATURE:
<221> NAME/KEY: MOD_RES
<222> LOCATION: 8, 17
<223> OTHER INFORMATION: Xaa = norleucine (Nle)
<220> FEATURE:
<221> NAME/KEY: AMIDATION
<222> LOCATION: 33

<400> SEQUENCE: 30

Ser Val Ser Glu Ile Gln Leu Xaa His Leu Gly Lys His Leu Asn Ser
1               5                   10                  15

Xaa Glu Arg Val Glu Trp Leu Arg Lys Lys Leu Gln Asp Val His Asn
                20                  25                  30

Tyr

<210> SEQ ID NO 31
<211> LENGTH: 33
<212> TYPE: PRT
<213> ORGANISM: Artificial Sequence
<220> FEATURE:
<223> OTHER INFORMATION: non-naturally occurring polypeptide
<220> FEATURE:
<221> NAME/KEY: MOD_RES
<222> LOCATION: 8, 17
<223> OTHER INFORMATION: Xaa = norleucine (Nle)
<220> FEATURE:
<221> NAME/KEY: AMIDATION
<222> LOCATION: 33

<400> SEQUENCE: 31

Ser Val Ser Glu Ile Gln Leu Xaa His Asn Gly Lys His Leu Asn Ser
1               5                   10                  15

Xaa Glu Arg Val Glu Trp Leu Arg Lys Lys Leu Gln Asp Val His Asn
                20                  25                  30

Tyr

<210> SEQ ID NO 32
<211> LENGTH: 33
<212> TYPE: PRT
<213> ORGANISM: Artificial Sequence
<220> FEATURE:
<223> OTHER INFORMATION: non-naturally occurring polypeptide
<220> FEATURE:
<221> NAME/KEY: MOD_RES
<222> LOCATION: 8, 17
<223> OTHER INFORMATION: Xaa = norleucine (Nle)
<220> FEATURE:
<221> NAME/KEY: AMIDATION
<222> LOCATION: 33

<400> SEQUENCE: 32

Ser Val Ser Glu Ile Gln Leu Xaa His Asn Leu Lys His Leu Asn Ser
1               5                   10                  15

Xaa Glu Arg Val Glu Trp Leu Arg Lys Lys Leu Gln Asp Val His Asn
                20                  25                  30

Tyr

<210> SEQ ID NO 33
<211> LENGTH: 33
<212> TYPE: PRT
<213> ORGANISM: Artificial Sequence
<220> FEATURE:
<223> OTHER INFORMATION: non-naturally occurring polypeptide
<220> FEATURE:

```
<221> NAME/KEY: MOD_RES
<222> LOCATION: 8, 17
<223> OTHER INFORMATION: Xaa = norleucine (Nle)
<220> FEATURE:
<221> NAME/KEY: AMIDATION
<222> LOCATION: 33

<400> SEQUENCE: 33

Ser Val Ser Glu Ile Gln Leu Xaa His Asn Leu Gly His Leu Asn Ser
 1               5                  10                  15

Xaa Glu Arg Val Glu Trp Leu Arg Lys Lys Leu Gln Asp Val His Asn
                20                  25                  30

Tyr

<210> SEQ ID NO 34
<211> LENGTH: 33
<212> TYPE: PRT
<213> ORGANISM: Artificial Sequence
<220> FEATURE:
<223> OTHER INFORMATION: non-naturally occurring polypeptide
<220> FEATURE:
<221> NAME/KEY: MOD_RES
<222> LOCATION: 8, 17
<223> OTHER INFORMATION: Xaa = norleucine (Nle)
<220> FEATURE:
<221> NAME/KEY: AMIDATION
<222> LOCATION: 33

<400> SEQUENCE: 34

Ser Val Ser Glu Ile Gln Leu Xaa His Asn Leu Gly Lys Leu Asn Ser
 1               5                  10                  15

Xaa Glu Arg Val Glu Trp Leu Arg Lys Lys Leu Gln Asp Val His Asn
                20                  25                  30

Tyr

<210> SEQ ID NO 35
<211> LENGTH: 33
<212> TYPE: PRT
<213> ORGANISM: Artificial Sequence
<220> FEATURE:
<223> OTHER INFORMATION: non-naturally occurring polypeptide
<220> FEATURE:
<221> NAME/KEY: MOD_RES
<222> LOCATION: 8, 17
<223> OTHER INFORMATION: Xaa = norleucine (Nle)
<220> FEATURE:
<221> NAME/KEY: AMIDATION
<222> LOCATION: 33

<400> SEQUENCE: 35

Ser Val Ser Glu Ile Gln Leu Xaa His Asn Leu Gly Lys His Asn Ser
 1               5                  10                  15

Xaa Glu Arg Val Glu Trp Leu Arg Lys Lys Leu Gln Asp Val His Asn
                20                  25                  30

Tyr

<210> SEQ ID NO 36
<211> LENGTH: 33
<212> TYPE: PRT
<213> ORGANISM: Artificial Sequence
<220> FEATURE:
<223> OTHER INFORMATION: non-naturally occurring polypeptide
<220> FEATURE:
<221> NAME/KEY: MOD_RES
<222> LOCATION: 8, 17
<223> OTHER INFORMATION: Xaa = norleucine (Nle)
<220> FEATURE:
```

```
<221> NAME/KEY: AMIDATION
<222> LOCATION: 33

<400> SEQUENCE: 36

Ser Val Ser Glu Ile Gln Leu Xaa His Asn Leu Gly Lys His Leu Ser
 1               5                  10                  15

Xaa Glu Arg Val Glu Trp Leu Arg Lys Lys Leu Gln Asp Val His Asn
            20                  25                  30

Tyr

<210> SEQ ID NO 37
<211> LENGTH: 33
<212> TYPE: PRT
<213> ORGANISM: Artificial Sequence
<220> FEATURE:
<223> OTHER INFORMATION: non-naturally occurring polypeptide
<220> FEATURE:
<221> NAME/KEY: MOD_RES
<222> LOCATION: 8, 17
<223> OTHER INFORMATION: Xaa = norleucine (Nle)
<220> FEATURE:
<221> NAME/KEY: AMIDATION
<222> LOCATION: 33

<400> SEQUENCE: 37

Ser Val Ser Glu Ile Gln Leu Xaa His Asn Leu Gly Lys His Leu Asn
 1               5                  10                  15

Xaa Glu Arg Val Glu Trp Leu Arg Lys Lys Leu Gln Asp Val His Asn
            20                  25                  30

Tyr

<210> SEQ ID NO 38
<211> LENGTH: 33
<212> TYPE: PRT
<213> ORGANISM: Artificial Sequence
<220> FEATURE:
<223> OTHER INFORMATION: non-naturally occurring polypeptide
<220> FEATURE:
<221> NAME/KEY: MOD_RES
<222> LOCATION: 8, 18
<223> OTHER INFORMATION: Xaa = norleucine (Nle)
<220> FEATURE:
<221> NAME/KEY: AMIDATION
<222> LOCATION: 33

<400> SEQUENCE: 38

Ser Val Ser Glu Ile Gln Leu Xaa His Asn Leu Gly Lys His Leu Asn
 1               5                  10                  15

Ser Xaa Arg Val Glu Trp Leu Arg Lys Lys Leu Gln Asp Val His Asn
            20                  25                  30

Tyr

<210> SEQ ID NO 39
<211> LENGTH: 33
<212> TYPE: PRT
<213> ORGANISM: Artificial Sequence
<220> FEATURE:
<223> OTHER INFORMATION: non-naturally occurring polypeptide
<220> FEATURE:
<221> NAME/KEY: MOD_RES
<222> LOCATION: 8, 18
<223> OTHER INFORMATION: Xaa = norleucine (Nle)
<220> FEATURE:
<221> NAME/KEY: AMIDATION
<222> LOCATION: 33

<400> SEQUENCE: 39
```

-continued

Ser Val Ser Glu Ile Gln Leu Xaa His Asn Leu Gly Lys His Leu Asn
 1               5                  10                  15

Ser Xaa Glu Val Glu Trp Leu Arg Lys Lys Leu Gln Asp Val His Asn
             20                  25                  30

Tyr

<210> SEQ ID NO 40
<211> LENGTH: 33
<212> TYPE: PRT
<213> ORGANISM: Artificial Sequence
<220> FEATURE:
<223> OTHER INFORMATION: non-naturally occurring polypeptide
<220> FEATURE:
<221> NAME/KEY: MOD_RES
<222> LOCATION: 8, 18
<223> OTHER INFORMATION: Xaa = norleucine (Nle)
<220> FEATURE:
<221> NAME/KEY: AMIDATION
<222> LOCATION: 33

<400> SEQUENCE: 40

Ser Val Ser Glu Ile Gln Leu Xaa His Asn Leu Gly Lys His Leu Asn
 1               5                  10                  15

Ser Xaa Glu Arg Glu Trp Leu Arg Lys Lys Leu Gln Asp Val His Asn
             20                  25                  30

Tyr

<210> SEQ ID NO 41
<211> LENGTH: 33
<212> TYPE: PRT
<213> ORGANISM: Artificial Sequence
<220> FEATURE:
<223> OTHER INFORMATION: non-naturally occurring polypeptide
<220> FEATURE:
<221> NAME/KEY: MOD_RES
<222> LOCATION: 8, 18
<223> OTHER INFORMATION: Xaa = norleucine (Nle)
<220> FEATURE:
<221> NAME/KEY: AMIDATION
<222> LOCATION: 33

<400> SEQUENCE: 41

Ser Val Ser Glu Ile Gln Leu Xaa His Asn Leu Gly Lys His Leu Asn
 1               5                  10                  15

Ser Xaa Glu Arg Val Trp Leu Arg Lys Lys Leu Gln Asp Val His Asn
             20                  25                  30

Tyr

<210> SEQ ID NO 42
<211> LENGTH: 33
<212> TYPE: PRT
<213> ORGANISM: Artificial Sequence
<220> FEATURE:
<223> OTHER INFORMATION: non-naturally occurring polypeptide
<220> FEATURE:
<221> NAME/KEY: MOD_RES
<222> LOCATION: 6, 10
<223> OTHER INFORMATION: Xaa = cyclohexylalanine (Cha)
<220> FEATURE:
<221> NAME/KEY: MOD_RES
<222> LOCATION: 7, 17
<223> OTHER INFORMATION: Xaa = norleucine (Nle)
<220> FEATURE:
<221> NAME/KEY: AMIDATION
<222> LOCATION: 33

<400> SEQUENCE: 42

Ser Val Ser Glu Ile Xaa Xaa His Asn Xaa Gly Lys His Leu Asn Ser
1               5                   10                  15

Xaa Glu Arg Val Glu Trp Leu Arg Lys Lys Leu Gln Asp Val His Asn
        20                  25                  30

Tyr

<210> SEQ ID NO 43
<211> LENGTH: 33
<212> TYPE: PRT
<213> ORGANISM: Artificial Sequence
<220> FEATURE:
<223> OTHER INFORMATION: non-naturally occurring polypeptide
<220> FEATURE:
<221> NAME/KEY: MOD_RES
<222> LOCATION: 7, 17
<223> OTHER INFORMATION: Xaa = norleucine (Nle)
<220> FEATURE:
<221> NAME/KEY: MOD_RES
<222> LOCATION: 10
<223> OTHER INFORMATION: Xaa = cyclohexylalanine (Cha)
<220> FEATURE:
<221> NAME/KEY: AMIDATION
<222> LOCATION: 33

<400> SEQUENCE: 43

Ser Val Ser Glu Ile Gln Xaa His Asn Xaa Gly Lys His Leu Asn Ser
1               5                   10                  15

Xaa Glu Arg Val Glu Trp Leu Arg Lys Lys Leu Gln Asp Val His Asn
        20                  25                  30

Tyr

<210> SEQ ID NO 44
<211> LENGTH: 33
<212> TYPE: PRT
<213> ORGANISM: Artificial Sequence
<220> FEATURE:
<223> OTHER INFORMATION: non-naturally occurring polypeptide
<220> FEATURE:
<221> NAME/KEY: MOD_RES
<222> LOCATION: 7, 10
<223> OTHER INFORMATION: Xaa = cyclohexylalanine (Cha)
<220> FEATURE:
<221> NAME/KEY: MOD_RES
<222> LOCATION: 8, 17
<223> OTHER INFORMATION: Xaa = norleucine (Nle)
<220> FEATURE:
<221> NAME/KEY: AMIDATION
<222> LOCATION: 33

<400> SEQUENCE: 44

Ser Val Ser Glu Ile Gln Xaa Xaa Asn Xaa Gly Lys His Leu Asn Ser
1               5                   10                  15

Xaa Glu Arg Val Glu Trp Leu Arg Lys Lys Leu Gln Asp Val His Asn
        20                  25                  30

Tyr

<210> SEQ ID NO 45
<211> LENGTH: 31
<212> TYPE: PRT
<213> ORGANISM: Artificial Sequence
<220> FEATURE:
<223> OTHER INFORMATION: non-naturally occurring polypeptide
<220> FEATURE:
<221> NAME/KEY: MOD_RES
<222> LOCATION: 7, 8
<223> OTHER INFORMATION: Xaa = cyclohexylalanine (Cha)
<220> FEATURE:

```
<221> NAME/KEY: AMIDATION
<222> LOCATION: 31

<400> SEQUENCE: 45

Ser Val Ser Glu Ile Gln Xaa Xaa Gly Lys His Leu Asn Ser Met Glu
1               5                   10                  15

Arg Val Glu Trp Leu Arg Lys Lys Leu Gln Asp Val His Asn Phe
            20                  25                  30

<210> SEQ ID NO 46
<211> LENGTH: 31
<212> TYPE: PRT
<213> ORGANISM: Artificial Sequence
<220> FEATURE:
<223> OTHER INFORMATION: non-naturally occurring polypeptide
<220> FEATURE:
<221> NAME/KEY: MOD_RES
<222> LOCATION: 7, 11
<223> OTHER INFORMATION: Xaa = cyclohexylalanine (Cha)
<220> FEATURE:
<221> NAME/KEY: AMIDATION
<222> LOCATION: 31

<400> SEQUENCE: 46

Ser Val Ser Glu Ile Gln Xaa Met His Asn Xaa Gly Lys His Leu Asn
1               5                   10                  15

Arg Val Glu Trp Leu Arg Lys Lys Leu Gln Asp Val His Asn Phe
            20                  25                  30

<210> SEQ ID NO 47
<211> LENGTH: 33
<212> TYPE: PRT
<213> ORGANISM: Artificial Sequence
<220> FEATURE:
<223> OTHER INFORMATION: non-naturally occurring polypeptide
<220> FEATURE:
<221> NAME/KEY: AMIDATION
<222> LOCATION: 33

<400> SEQUENCE: 47

Ala Val Ser Glu Ile Gln Leu His Asp Lys Gly Lys Ser Ile Gln Asp
1               5                   10                  15

Leu Arg Arg Arg Phe Trp Leu His His Leu Ile Ala Glu Ile His Thr
            20                  25                  30

Ala

<210> SEQ ID NO 48
<211> LENGTH: 33
<212> TYPE: PRT
<213> ORGANISM: Artificial Sequence
<220> FEATURE:
<223> OTHER INFORMATION: non-naturally occurring polypeptide
<220> FEATURE:
<221> NAME/KEY: AMIDATION
<222> LOCATION: 33

<400> SEQUENCE: 48

Ala Val Ser Glu Ile Gln Leu His Asp Lys Gly Lys Ser Ile Gln Asp
1               5                   10                  15

Leu Arg Arg Arg Phe Phe Leu His His Leu Ile Ala Glu Ile His Thr
            20                  25                  30

Ala

<210> SEQ ID NO 49
<211> LENGTH: 33
```

```
<212> TYPE: PRT
<213> ORGANISM: Artificial Sequence
<220> FEATURE:
<223> OTHER INFORMATION: non-naturally occurring polypeptide
<220> FEATURE:
<221> NAME/KEY: AMIDATION
<222> LOCATION: 33

<400> SEQUENCE: 49

Ala Val Ser Glu His Gln Leu His Asp Lys Gly Lys Ser Ile Gln Asp
 1               5                  10                  15
Leu Arg Arg Arg Phe Trp Leu His His Leu Ile Ala Glu Ile His Thr
            20                  25                  30
Ala

<210> SEQ ID NO 50
<211> LENGTH: 33
<212> TYPE: PRT
<213> ORGANISM: Artificial Sequence
<220> FEATURE:
<223> OTHER INFORMATION: non-naturally occurring polypeptide
<220> FEATURE:
<221> NAME/KEY: AMIDATION
<222> LOCATION: 33

<400> SEQUENCE: 50

Ala Val Ser Glu Ile Gln Leu Leu His Asp Lys Gly Lys Ser Ile Gln
 1               5                  10                  15
Asp Arg Arg Arg Phe Phe Leu His His Leu Ile Ala Glu Ile His Thr
            20                  25                  30
Ala

<210> SEQ ID NO 51
<211> LENGTH: 33
<212> TYPE: PRT
<213> ORGANISM: Artificial Sequence
<220> FEATURE:
<223> OTHER INFORMATION: non-naturally occurring polypeptide
<220> FEATURE:
<221> NAME/KEY: AMIDATION
<222> LOCATION: 33

<400> SEQUENCE: 51

Ala Val Ser Glu Ile Gln Leu Leu His Asp Lys Gly Lys Ser Ile Gln
 1               5                  10                  15
Asp Arg Arg Arg Phe Trp Leu His His Leu Ile Ala Glu Ile His Thr
            20                  25                  30
Ala

<210> SEQ ID NO 52
<211> LENGTH: 33
<212> TYPE: PRT
<213> ORGANISM: Artificial Sequence
<220> FEATURE:
<223> OTHER INFORMATION: non-naturally occurring polypeptide
<220> FEATURE:
<221> NAME/KEY: AMIDATION
<222> LOCATION: 33

<400> SEQUENCE: 52

Ala Val Ser Glu His Gln Leu Leu His Asp Lys Gly Lys Ser Ile Gln
 1               5                  10                  15
Asp Arg Arg Arg Phe Trp Leu His His Leu Ile Ala Glu Ile His Thr
            20                  25                  30
```

```
<210> SEQ ID NO 53
<211> LENGTH: 34
<212> TYPE: PRT
<213> ORGANISM: Artificial Sequence
<220> FEATURE:
<223> OTHER INFORMATION: non-naturally occurring polypeptide
<220> FEATURE:
<221> NAME/KEY: AMIDATION
<222> LOCATION: 34

<400> SEQUENCE: 53

Ser Val Ser Glu Ile Gln Leu Met His Asn Leu Gly Lys His Leu Asn
 1               5                  10                  15

Ser Met Glu Arg Val Glu Trp Leu Arg Lys Lys Leu Gln Asp Val His
                20                  25                  30

Asn Phe
```

PTH2 RECEPTOR SELECTIVE COMPOUNDS

STATEMENT AS TO GOVERNMENT FUNDING

This invention was supported in part by Government funding, NIDDK Research Grant DK-4790, and the Government, therefore, may have certain rights in the invention.

CROSS REFERENCE TO RELATED APPLICATIONS

This application is a United States national filing under 35 U.S.C. §371 of international (PCT) application No. PCT/US99/09521 with an international filing date of May 3, 1999, which claims the benefit of U.S. patent application Ser. No. 09/072,956, filed May 5, 1998, now abandoned.

BACKGROUND OF THE ART

This invention relates to a series of PTH and PTHrP analogues that selectively bind to PTH2 receptors and as such may be useful in treating abnormal CNS functions; abnormal pancreatic functions; divergence from normal mineral metabolism and homeostasis; male infertility; regulation of abnormal blood pressure; and hypothalmic disease, to name a few potential uses.

An alternate parathyroid hormone (PTH) receptor, designated as PTH2 receptor, has been identified in rat and human brain. This receptor is selectively activated by PTH-(1-34) (SEQ ID NO:1), but not PTH-related protein PTHrP-(1-34) (SEQ ID NO:2), which has the same calcium-mobilizing activities as PTH-(1-34) (SEQ ID NO:1). Both PTH and PTHrP share a common G protein-coupled receptor, termed the PTH/PTHrP receptor. The PTH2 receptor is localized predominantly in the brain and pancreas, in contrast to PTH/PTHrP receptor, which is primarily localized in bone and the kidney, the principal target tissue for PTH action. Parathyroid hormone (PTH) is the principal physiological regulator of calcium levels in the blood (Chorev, M., Rosenblatt, M., 1994, Structure function analysis of parathyroid hormone and parathyroid hormone-related protein, Bilezikian, J. P., Marcus, R., Levine, M., (eds) The Parathyroids: Basic and Clinical Concepts. Raven Press, New York, pp 139-156; Juppner, H., et al., 1991, Science, 254:1024-1026; and Martin, T. J., et al., 1991, Crit. Rev. Biochem. Mol. Biol. 26:377-395). PTH-related protein (PTHrP) was originally identified as the agent responsible for the paraneoplastic syndrome of humoral hypercalcemia of malignancy (Suva, L. J., et al., 1987, Science, 237:893-896 and Orloff, J. J., et al., 1994, Endocrinol. Rev. 15:40-60). PTH and PTHrP are products of distinct, yet evolutionary-related genes. PTH and PTHrP show sequence similarities only in the N-terminal 13 amino acids, 8 of which are identical (Abou-Samra A B, et al., 1992, Proc. Natl. Sci. Acad. USA, 89:2732-2736). However, the expression pattern and physiological role of these two molecules are remarkably different. PTH has a highly restricted pattern of expression and acts as a classical endocrine hormone, whereas PTHrP is expressed in a wide variety of normal tissues and functions in a predominantly autocrine/paracrine fashion (Urena, P., et al., 1993, Endocrinology, 133:617-623; Lee, K., et al., 1995, Endocrinology, 136:453-463; and Martin, T. J., et al., 1995, Miner. Electrolyte Metab., 21:123-128). More recently, PTHrP has been shown to play a fundamental role in embryonic differentiation of bone and cartilage development.

PTH and PTHrP exert their wide-ranging effects via a common receptor located on the surface of target cells (Juppner, H., et al., 1988, J. Biol. Chem., 263:1071-1078; Shigeno, C., et al., 1988, J. Biol. Chem., 263:18369-18377). The PTH/PTHrP receptor is a member of a subfamily of G protein-coupled receptor superfamily, which includes the receptors for glucagon, growth hormone-releasing hormone (GHRH), vasoactive intestinal peptide (VIP), glucagon-like peptide 1 (GLP-1), gastric inhibitory polypeptide (GIP), secretin, pituitary adenylate cyclase-activating polypeptide (PACAP), calcitonin, and corticotropin-releasing factor (CRF) (Segre, G., et al., 1993, Trends Endocrinol. Metab. 4:309-314). The PTH/PTHrP receptor recognizes the N-terminal 1-34 regions of both ligands (Schipani, E., et al., 1993, Endocrinology, 132:2157-2165) and is particularly abundant in classical PTH target tissues such as bone and kidney (Urena, P., et al., 1993 Endocrinology, 133:35-38). Ligand binding to the PTH/PTHrP receptor can activate at least two signaling pathways; the adenylyl cyclase-cAMP-protein kinase A pathway (Partridge, N C, et al., 1981, Endocrinology 108:220-225), and the inositol trisphosphate-cytosolic calcium-protein kinase C pathway (Abou-Samra, A-B., et al., 1989, Endocrinology 124:1107-1113).

An homologous receptor for PTH, designated the PTH2 receptor, has been identified and partially characterized (Behar, V., et al., 1996, Endocrinology, 137:2748-2757; Gardella, T. J., et al., 1996, The J. Biol. Chem., 271:19888-19893; Behar, V., et al., 1996, Endocrinology, 137:4217-4224; and Usdin, T. B., et al., 1997, Endocrinology, 138:831-834). Amongst the seven transmembrane G protein-coupled receptors, the PTH2 receptor is most similar in sequence to the PTH/PTHrP receptor (51% of the amino acid sequence identify). Interestingly, PTH2 receptor mRNA is not detected in bone or osteosarcoma cell lines, but is expressed in a number of tissues including the exocrine pancreas, lung, heart, vasculature, and epididymis, and is most abundant in the brain (Usdin, T. B., et al., 1996, Endocrinology, 137:4285-4297). Unlike the PTH/PTHrP receptor, which binds and is activated by both PTH-(1-34) (SEQ ID NO:1) and PTHrP-(1-34) (SEQ ID NO:2), the PTH2 receptor binds and is activated only by PTH-(1-34) (SEQ ID NO:1). PTHrP (7-34) (SEQ ID NO:2) was found to recognize PTH2 receptor and weakly activate it. Moreover, His$^5$ in PTHrP was identified as the "specificity switch" for the PTH2 receptor. Swapping a single amino acid, His$^5$ from PTHrP, with Ile$^5$ from PTH, resulted in a PTHrP analogue, Ile$^5$-PTHrP-(1-34) NH$_2$ (SEQ ID NO:3), which acts as a PTH-2 receptor agonist. Hence, the single amino acid switch converts inactive PTHrP into a potent PTH2 receptor agonist. But while PTHrP (SEQ ID NO:3) binds and activates both receptors, PTH/PTHrP and PTH2, it is not a selective PTH2 agonist. In transient heterologous (with respect to species) expression systems, others have found an additional contribution to hPTH2 receptor selectivity by Trp$^{23}$ (Gardella et al., JBC 1996, 271:19888-19893). Like the PTH/PTHrP receptor, PTH binding leads to PTH2 receptor-mediated activation of both cAMP and intracellular signaling pathways.

The physiological function of the PTH2 receptor because of its high abundance and distribution in the brain suggests that it may act as a neurotransmitter receptor. PTH has been found in the central nervous system (CNS) (Harvey, S., et al., 1993, J. Endocrinol. 139:353-361), therefore, it is possible that endogenous PTH2 receptor specific ligands, which are distinct from PTH, do exist in the CNS. Recently, Usdin reported the isolation of "PTH2 receptor binding activity" from the hypothalamus which was immunologically distinct from PTH.

PCT Application Number PCT/US97/13360, published as PCT Publication Number WO 98/04591, discloses the use of certain PTHrP analogs which are PTH2 receptor agonists or antagonists.

U.S. Pat. No. 5,723,577, issued Mar. 3, 1998, discloses certain PTH and PTHrP analogues. U.S. application Nos. 08/779,768 and 08/813,534, filed Jan. 7, 1997 and Mar. 7, 1997, respectively, disclose further PTH and PTHrP analogs.

The development of specific ligands which activate the PTH2 receptor but not the PTH/PTHrP receptor, would be highly useful in defining the physiological roles of the PTH2 receptor and its potential involvement in certain pathological states. We have discovered a series of PTH2 receptor-selective PTH analogues which interact selectively with the human PTH2 receptor and are practically devoid of PTH/PTHrP receptor interaction. The compounds of the present invention are not only selective toward a receptor subtype but also signal specifically through the stimulation of $[Ca^{+2}]_i$ transients. Therefore, the compounds of the present invention are receptor subtype and signaling pathway selective.

SUMMARY OF THE INVENTION

In one aspect, this invention provides a PTH analogue or a truncated PTH analogue or a pharmaceutically acceptable salt thereof that selectively binds to the PTH2 receptor. A preferred PTH analogue or a truncated PTH analogue or a pharmaceutically acceptable salt thereof is where the analogue is a selective PTH2 receptor agonist. Another preferred PTH analogue or a truncated PTH analogue or a pharmaceutically acceptable salt thereof is where the analogue is a selective PTH2 receptor antagonist.

A more preferred PTH analogue that selectively binds to the PTH2 receptor is an analogue of formula (I), $(R^1R^2)$-$A^1$-$A^2$-$A^3$-$A^4$-$A^5$-$A^6$-$A^7$-$A^8$-$A^9$-$A^{10}$-$A^{11}$-$A^{12}$-$A^{13}$-$A^{14}$-$A^{15}$-$A^{16}$-$A^{17}$-$A^{18}$-$A^{19}$-$A^{20}$-$A^{21}$-$A^{22}$-$A^{23}$-$A^{24}$-$A^{25}$-$A^{26}$-$A^{27}$-$A^{28}$-$A^{29}$-$A^{30}$-$A^{31}$-$A^{32}$-$A^{33}$-$A^{34}$-$A^{35}$-$A^{36}$-$A^{37}$-$A^{38}$-$R^3$, (I)

or a pharmaceutically-acceptable salt thereof wherein
$A^1$ is a hydrophilic or a lipophilic amino acid;
$A^2$ is a lipophilic amino acid;
$A^3$ is a hydrophilic or a lipophilic amino acid;
$A^4$ is a hydrophilic amino acid;
$A^5$ is a hydrophilic or a lipophilic amino acid;
$A^6$ is a hydrophilic amino acid or is deleted;
$A^7$ is a hydrophilic or a lipophilic amino acid or is deleted;
$A^8$ is a lipophilic amino acid or is deleted;
$A^9$ is a hydrophilic amino acid or is deleted;
$A^{10}$ is a hydrophilic amino acid or is deleted;
$A^{11}$ is a hydrophilic or a lipophilic amino acid or is deleted;
$A^{12}$ is a hydrophilic or a lipophilic amino acid or is deleted;
$A^{13}$ is a hydrophilic amino acid;
$A^{14}$ is a hydrophilic amino acid or is deleted;
$A^{15}$ is a lipophilic amino acid or is deleted;
$A^{16}$ is a hydrophilic or a lipophilic amino acid or is deleted;
$A^{17}$ is a hydrophilic or a lipophilic amino acid or is deleted;
$A^{18}$ is a lipophilic amino acid or is deleted;
$A^{19}$ is a hydrophilic or a lipophilic amino acid or is deleted;
$A^{20}$ is a hydrophilic amino acid or is deleted;
$A^{21}$ is a hydrophilic or a lipophilic amino acid or is deleted;
$A^{22}$ is a lipophilic or a hydrophilic amino acid or is deleted;
$A^{23}$ is a hydrophilic or a lipophilic amino acid;
$A^{24}$ is a hydrophilic or a lipophilic amino acid;
$A^{25}$ is a hydrophilic amino acid;
$A^{26}$ is a hydrophilic amino acid;
$A^{27}$ is a lipophilic or a hydrophilic amino acid;
$A^{28}$ is a lipophilic amino acid;
$A^{29}$ is a lipophilic or a hydrophilic amino acid;
$A^{30}$ is a hydrophilic or a lipophilic amino acid;
$A^{31}$ is a lipophilic or a hydrophilic amino acid or is deleted;
$A^{32}$ is a hydrophilic amino acid or is deleted;
$A^{33}$ is a hydrophilic amino acid or is deleted;
$A^{34}$ is a lipophilic amino acid or is deleted;
$A^{35}$ is a lipophilic amino acid or is deleted;
$A^{36}$ is a lipophilic or a hydrophilic amino acid or is deleted;
$A^{37}$ is a lipophilic amino acid or is deleted;
$A^{38}$ is a lipophilic or a hydrophilic amino acid or is deleted;
$R^1$ and $R^2$ are each independently selected from the group consisting of H, $(C_1$-$C_{30})$alkyl, $(C_2$-$C_{30})$alkenyl, phenyl-$(C_1$-$C_{30})$alkyl, naphthyl$(C_1$-$C_{30})$alkyl, hydroxy$(C_1$-$C_{30})$alkyl, hydroxy$(C_2$-$C_{30})$alkenyl, hydroxy-phenyl$(C_1$-$C_{30})$alkyl or hydroxy-naphthyl $(C_1$-$C_{30})$alkyl;
or one of $R^1$ or $R^2$ is $COE^1$ where $E^1$ is $(C_1$-$C_{30})$alkyl, $(C_2$-$C_{30})$alkenyl, phenyl$(C_1$-$C_{30})$alkyl, naphthyl$(C_1$-$C_{30})$alkyl, hydroxy$(C_1$-$C_{30})$alkyl, hydroxy$(C_2$-$C_{30})$alkenyl, hydroxy-phenyl$(C_1$-$C_{30})$alkyl or hydroxy-naphthyl$(C_1$-$C_{30})$alkyl; and
$R^3$ is OH, $NH_2$, $(C_1$-$C_{30})$alkoxy or $NH$-$Y$-$CH_2$-$Z$, where Y is a $(C_1$-$C_{30})$ hydrocarbon moiety and Z is $CO_2H$ or $CONH_2$;

provided that the compound is not PTH(1-34)$R^3$ (SEQ ID NO:4), PTH(1-35)$R^3$ (SEQ ID NO:5), PTH(1-36)$R^3$ (SEQ ID NO:6), PTH(1-37)$R^3$ (SEQ ID NO:7); or PTH(1-38)$R^3$ (SEQ ID NO:8).

Another preferred group of PTH analogues that selectively binds to the PTH2 receptor is an analogue of formula (II), $(R^1R^2)$-$A^1$-$A^2$-$A^3$-$A^4$-$A^5$-$A^6$-$A^7$-$A^8$-$A^9$-$A^{10}$-$A^{11}$-$A^{12}$-$A^{13}$-$A^{14}$-$A^{15}$-$A^{16}$-$A^{17}$-$A^{18}$-$A^{19}$-$A^{20}$-$A^{21}$-$A^{22}$-$A^{23}$-$A^{24}$-$A^{25}$-$A^{26}$-$A^{27}$-$A^{28}$-$A^{29}$-$A^{30}$-$A^{31}$-$A^{32}$-$A^{33}$-$A^{34}$-$A^{35}$-$A^{36}$-$A^{37}$-$A^{38}$-$R^3$, (II)

or a pharmaceutically-acceptable salt thereof wherein
$A^1$ is Ser, Ala, Dap, Thr, Aib or is deleted;
$A^2$ is Val, Leu, Ile, Phe, Nle, β-Nal, Aib, p-X-Phe, Acc, Cha, Met or is deleted;
$A^3$ is Ser, Thr, Aib or is deleted;
$A^4$ is Glu, Asp or is deleted;
$A^5$ is Leu, Val, Nle, Ile, Cha, β-Nal, Trp, Pal, Acc, Phe, p-X-Phe or is deleted;
$A^6$ is Gln, a hydrophilic amino acid or is deleted;
$A^7$ is Leu, Val, Nle, Ile, Cha, β-Nal, Trp, Pal, Acc, Phe, p-X-Phe, a lipophilic amino acid, or is deleted;
$A^8$ is Met, Nva, Leu, Val, Ile, Cha, Acc, Nle, p-X-Phe, Phe, β-Nal, Bpa, a lipophilic amino acid or is deleted;
$A^9$ is His, a hydrophilic amino acid or is deleted;
$A^{10}$ is Asn, a hydrophilic amino acid or is deleted;
$A^{11}$ is Leu, Val, Nle, Ile, Cha, β-Nal, Trp, Pal, Acc, Phe, p-X-Phe, a hydrophilic amino acid or is deleted;
$A^{12}$ is Gly, Acc, Aib, or is deleted;
$A^{13}$ is Lys, Arg or HN—CH$((CH_2)_n$NH—$R^4)$—C(O);
$A^{14}$ is His or is deleted;
$A^{15}$ is Leu, Val, Nle, Ile, Cha, β-Nal, Trp, Pal, Acc, Phe, p-X-Phe or is deleted;
$A^{16}$ is Ser, Asn, Ala, Aib or is deleted;
$A^{17}$ is Ser, Thr, Aib or is deleted;
$A^{18}$ is Met, Nva, Leu, Val, Ile, Nle, p-X-Phe, Phe, β-Nal, Acc, Cha, Aib or is deleted;
$A^{19}$ is Glu, Aib or is deleted;
$A^{20}$ is Arg, Lys, HN—CH$((CH_2)_n$NH—$R^4)$—C(O) or is deleted;
$A^{21}$ is Val, Leu, Ile, Phe, Nle, β-Nal, Aib, p-X-Phe, Acc, Cha, Met or is deleted;
$A^{22}$ is Acc, Aib, Glu or is deleted;

$A^{23}$ is Trp, Acc, Phe, p-X-Phe, Aib, β-Nal or Cha;
$A^{24}$ is Leu, Acc, Ile, Val, Phe, β-Nal, Nle, Aib, p-X-Phe or Cha;
$A^{25}$ is Arg, Lys or HN—CH(($CH_2$)$_n$NH—$R^4$)—C(O);
$A^{26}$ is Arg, Lys or HN—CH(($CH_2$)$_n$NH—$R^4$)—C(O);
$A^{27}$ is Lys, Aib, Leu, hArg, Gln, Acc, Arg, Cha, Nle, Ile, Val, Phe, β-Nal, or p-X-Phe, where the Lys is optionally substituted on the ε-amino group by an acyl group;
$A^{28}$ is Leu, Acc, Cha, Ile, Val, Phe, Nle, β-Nal, Aib or p-X-Phe;
$A^{29}$ is Gln, Acc or Aib;
$A^{30}$ is Asp, Lys, Arg or is deleted;
$A^{31}$ is Val, Leu, Nle, Acc, Cha, Phe, Ile, β-Nal, Aib, p-X-Phe or is deleted;
$A^{32}$ is His or is deleted;
$A^{33}$ is Asn or is deleted;
$A^{34}$ is Phe, Tyr, Amp, Aib, β-Nal, Cha, Nle, Leu, Ile, Acc, p-X-Phe or is deleted;
$A^{35}$ is Val, Leu, Nle, Acc, Cha, Phe, Ile, β-Nal, Aib, p-X-Phe or is deleted;
$A^{36}$ is Ala, Val, Aib, Acc, Nva, Abu or is deleted;
$A^{37}$ is Leu, Val, Nle, Ile, Cha, β-Nal, Trp, Pal, Acc, Phe, p-X-Phe, a lipophilic amino acid, or is deleted;
$A^{38}$ is Gly, Acc, Aib, or is deleted;
where X for each occurrence is independently selected from the group consisting of OH, a halo and $CH_3$;
$R^1$ and $R^2$ are each independently selected from the group consisting of H, ($C_1$-$C_{30}$)alkyl, ($C_2$-$C_{30}$)alkenyl, phenyl-($C_1$-$C_{30}$)alkyl, naphthyl($C_1$-$C_{30}$)alkyl, hydroxy($C_1$-$C_{30}$)alkyl, hydroxy($C_2$-$C_{30}$)alkenyl, hydroxy-phenyl($C_1$-$C_{30}$)alkyl or hydroxy-naphthyl($C_1$-$C_{30}$)alkyl;
or one of $R^1$ or $R^2$ is $COE^1$ where $E^1$ is ($C_1$-$C_{30}$)alkyl, ($C_2$-$C_{30}$)alkenyl, phenyl($C_1$-$C_{30}$)alkyl, naphthyl($C_1$-$C_{30}$)alkyl, hydroxy($C_1$-$C_{30}$)alkyl, hydroxy($C_2$-$C_{30}$)alkenyl, hydroxy-phenyl($C_1$-$C_{30}$)alkyl or hydroxy-naphthyl($C_1$-$C_{30}$)alkyl;
$R^3$ is OH, $NH_2$, ($C_1$-$C_{30}$)alkoxy or NH-Y-$CH_2$-Z, where Y is a ($C_1$-$C_{30}$) hydrocarbon moiety and Z is $CO_2$H or $CONH_2$;
n for each occurrence is independently an integer from 1 to 5; and
$R^4$ for each occurrence is independently ($C_1$-$C_{30}$)alkyl, ($C_1$-$C_{30}$)acyl or —C((NH)($NH_2$));

provided that the compound is not PTH(1-34)$R^3$ (SEQ ID NO:4), PTH(1-35)$R^3$ (SEQ ID NO:5), PTH(1-36)$R^3$ (SEQ ID NO:6), PTH(1-37)$R^3$ (SEQ ID NO:7), or PTH(1-38)$R^3$ (SEQ ID NO:8).

In another respect, this invention provides a PTHrP analogue that selectively binds to the PTH2 receptor of the formula (IV), ($R^1R^2$)-$A^1$-$A^2$-$A^3$-$A^4$-$A^5$-$A^6$-$A^7$-$A^8$-$A^9$-$A^{10}$-$A^{11}$-$A^{12}$-$A^{13}$-$A^{14}$-$A^{15}$-$A^{16}$-$A^{17}$-$A^{18}$-$A^{19}$-$A^{20}$-$A^{21}$-$A^{22}$-$A^{23}$-$A^{24}$-$A^{25}$-$A^{26}$-$A^{27}$-$A^{28}$-$A^{29}$-$A^{30}$-$A^{31}$-$A^{32}$-$A^{33}$-$A^{34}$-$A^{35}$-$A^{36}$-$A^{37}$-$A^{38}$-$R^3$, (IV)

or a pharmaceutically acceptable salt thereof, wherein
$A^1$ is Ala, Ser, Dap, Thr, Aib or is deleted;
$A^2$ is Val or is deleted;
$A^3$ is Ser, Aib, Thr or is deleted;
$A^4$ is Glu, Asp or is deleted;
$A^5$ is His, Ile, Acc, Val, Nle, Phe, Leu, p-X-Phe, β-Nal, Aib, Cha or is deleted;
$A^6$ is Gln, a hydrophilic amino acid or is deleted;
$A^7$ is Leu, Val, Cha, Nle, β-Nal, Trp, Pal, Acc, Phe, p-X-Phe, Aib, a lipophilic amino acid or is deleted;
$A^8$ is Leu, Met, Acc, Cha, Aib, Nle, Phe, Ile, Val, β-Nal, p-X-Phe, a lipophilic amino acid or is deleted;
$A^9$ is His, a hydrophilic amino acid or is deleted;
$A^{10}$ is Asp, Asn, a hydrophilic amino acid or is deleted;
$A^{11}$ is Lys, Arg, Leu, Cha, Aib, p-X-Phe, Ile, Val, Nle, Acc, Phe, β-Nal, HN—CH(($CH_2$)$_n$NH—$R^4$)—C(O), a lipophilic D-amino acid, a hydrophilic amino acid or is deleted;
$A^{12}$ is Gly, Acc, Aib, or is deleted;
$A^{13}$ is Lys, Arg, HN—CH(($CH_2$)$_n$NH—$R^4$)—C(O) or is deleted;
$A^{14}$ is Ser, His or is deleted;
$A^{15}$ is Ile, Acc, Cha, Leu, Phe, Nle, β-Nal, Trp, p-X-Phe, Val, Aib or is deleted;
$A^{16}$ is Gln, Aib or is deleted;
$A^{17}$ is Asp, Aib or is deleted;
$A^{18}$ is Leu, Aib, Acc, Cha, Phe, Ile, Nle, β-Nal, Val, p-X-Phe or is deleted;
$A^{19}$ is Arg, Lys, Aib, HN—CH(($CH_2$)$_n$NH—$R^4$)—C(O) or is deleted;
$A^{20}$ is Arg, Lys, HN—CH(($CH_2$)$_n$NH—$R^4$)—C(O) or is deleted;
$A^{21}$ is Arg, Lys, HN—CH(($CH_2$)$_n$NH—$R^4$)—C(O) or is deleted;
$A^{22}$ is Phe, Glu, Aib, Acc, p-X-Phe, β-Nal, Val, Leu, Ile, Nle or Cha;
$A^{23}$ is Phe, Leu, Lys, Acc, Cha, β-Nal, Aib, Nle, Ile, p-X-Phe, Val or Trp;
$A^{24}$ is Leu, Lys, Acc, Nle, Ile, Val, Phe, β-Nal, Aib, p-X-Phe, Arg or Cha;
$A^{25}$ is His, Lys, Aib, Acc, Arg or Glu;
$A^{26}$ is His, Aib, Acc, Arg or Lys;
$A^{27}$ is Leu, Lys, Acc, Arg, Ile, Val, Phe, Aib, Nle, β-Nal, p-X-Phe or Cha;
$A^{28}$ is Ile, Leu, Lys, Acc, Cha, Val, Phe, p-X-Phe, Nle, β-Nal, Aib or is deleted;
$A^{29}$ is Ala, Gln, Acc, Aib or is deleted;
$A^{30}$ is Glu, Leu, Nle, Cha, Aib, Acc, Lys, Arg or is deleted;
$A^{31}$ is Ile, Leu, Cha, Lys, Acc, Phe, Val, Nle, β-Nal, Arg or is deleted;
$A^{32}$ is His or is deleted;
$A^{33}$ is Thr, Ser or is deleted;
$A^{34}$ is Ala, Phe, Tyr, Cha, Val, Ile, Leu, Nle, β-Nal, Aib, Acc or is deleted;
$A^{35}$ is Glu, Asp or is deleted;
$A^{36}$ is Ile, Acc, Cha, Leu, Phe, Nle, β-Nal, Trp, p-X-Phe, Val, Aib or is deleted;
$A^{37}$ is Arg, Lys, HN—CH(($CH_2$)$_n$NH—$R^4$)—C(O) or is deleted;
$A^{38}$ is Ala, Phe, Tyr, Cha, Val, Ile, Leu, Nle, β-Nal, Aib, Acc or is deleted;
$R^1$ and $R^2$ are each independently selected from the group consisting of H, ($C_1$-$C_{30}$)alkyl, ($C_2$-$C_{30}$)alkenyl, phenyl-($C_1$-$C_{30}$)alkyl, naphthyl($C_1$-$C_{30}$)alkyl, hydroxy($C_1$-$C_{30}$)alkyl, hydroxy($C_2$-$C_{30}$)alkenyl, hydroxy-phenyl($C_1$-$C_{30}$)alkyl or hydroxy-naphthyl($C_1$-$C_{30}$)alkyl;
or one of $R^1$ or $R^2$ is $COE^1$ where $E^1$ is ($C_1$-$C_{30}$)alkyl, ($C_2$-$C_{30}$)alkenyl, phenyl($C_1$-$C_{30}$)alkyl, naphthyl($C_1$-$C_{30}$)alkyl, hydroxy($C_1$-$C_{30}$)alkyl, hydroxy($C_2$-$C_{30}$)alkenyl, hydroxy-phenyl($C_1$-$C_{30}$)alkyl or hydroxy-naphthyl($C_1$-$C_{30}$)alkyl;
$R^3$ is OH, $NH_2$, ($C_1$-$C_{30}$)alkoxy or NH-Y-$CH_2$-Z, where Y is a ($C_1$-$C_{30}$) hydrocarbon moiety and Z is $CO_2$H or $CONH_2$;
n for each occurrence is independently an integer from 1 to 5; and
$R^4$ for each occurrence is independently ($C_1$-$C_{30}$)alkyl, ($C_1$-$C_{30}$)acyl or —C((NH)($NH_2$));

provided that the compound is not PTHrP(1-34)R³ (SEQ ID NO:9), PTHrP(1-35)R³ (SEQ ID NO:10), PTHrP(1-36)R³ (SEQ ID NO:11), PTHrP(1-37)R³ (SEQ ID NO:12) or PTHrP(1-38)R³ (SEQ ID NO:13), and further provided that the compound is not [Ile⁵, Trp²³] PTHrP(1-36) (SEQ ID NO:14) or [Trp²³] PTHrP(1-36) (SEQ ID NO:15).

In another aspect, this invention provides a method of selectively binding the PTH2 receptor which comprises administering to a patient in need thereof an effective amount of a PTH analogue or a truncated PTH analogue or a pharmaceutically acceptable salt thereof that selectively binds to a PTH2 receptor.

In another aspect, this invention provides a method of selectively eliciting an agonist response from the PTH2 receptor which comprises administering to a patient in need thereof an effective amount of a PTH analogue or a truncated PTH analogue or a pharmaceutically acceptable salt thereof which is a selective PTH2 receptor agonist.

In another aspect, this invention provides a method of selectively eliciting an antagonist response from the PTH2 receptor which comprises administering to a patient in need thereof an effective amount of a PTH analogue or a truncated PTH analogue or a pharmaceutically acceptable salt thereof which is a selective PTH2 receptor antagonist.

In yet another aspect, this invention provides a compound of the formula (III), $(R^1R^2)$-$A^1$-$A^2$-$A^3$-$A^4$-$A^5$-$A^6$-$A^7$-$A^8$-$A^9$-$A^{10}$-$A^{11}$-$A^{12}$-$A^{13}$-$A^{14}$-$A^{15}$-$A^{16}$-$A^{17}$-$A^{18}$-$A^{19}$-$A^{20}$-$A^{21}$-$A^{22}$-$A^{23}$-$A^{24}$-$A^{25}$-$A^{26}$-$A^{27}$-$A^{28}$-$A^{29}$-$A^{30}$-$A^{31}$-$A^{32}$-$A^{33}$-$A^{34}$-$A^{35}$-$A^{36}$-$A^{37}$-$A^{38}$-$R^3$, (III)

or a pharmaceutically-acceptable salt thereof wherein
$A^1$ is Ser, Ala, Dap, Thr, Aib or is deleted;
$A^2$ is Val, Leu, Ile, Phe, Nle, β-Nal, Aib, p-X-Phe, Acc, Cha, Met or is deleted;
$A^3$ is Ser, Thr, Aib or is deleted;
$A^4$ is Glu, Asp or is deleted;
$A^5$ is Leu, Val, Nle, Ile, Cha, β-Nal, Trp, Pal, Acc, Phe, p-X-Phe or is deleted;
$A^6$ is Gln, a hydrophilic amino acid or is deleted;
$A^7$ is Leu, Val, Nle, Ile, Cha, β-Nal, Trp, Pal, Acc, Phe, p-X-Phe, a lipophilic amino acid, or is deleted;
$A^8$ is Met, Nva, Leu, Val, Ile, Cha, Acc, Nle, p-X-Phe, Phe, β-Nal, Bpa, a lipophilic amino acid or is deleted;
$A^9$ is His, a hydrophilic amino acid or is deleted;
$A^{10}$ is Asn, a hydrophilic amino acid or is deleted;
$A^{11}$ is Leu, Val, Nle, Ile, Cha, β-Nal, Trp, Pal, Acc, Phe, p-X-Phe, a hydrophilic amino acid or is deleted;
$A^{12}$ is Gly, Acc, Aib, or is deleted;
$A^{13}$ is Lys, Arg or HN—CH($(CH_2)_n$NH—$R^4$)—C(O);
$A^{14}$ is His or is deleted;
$A^{15}$ is Leu, Val, Nle, Ile, Cha, β-Nal, Trp, Pal, Acc, Phe, p-X-Phe or is deleted;
$A^{16}$ is Ser, Asn, Ala, Aib or is deleted;
$A^{17}$ is Ser, Thr, Aib or is deleted;
$A^{18}$ is Met, Nva, Leu, Val, Ile, Nle, p-X-Phe, Phe, β-Nal, Acc, Cha, Aib or is deleted;
$A^{19}$ is Glu, Aib or is deleted;
$A^{20}$ is Arg, Lys, HN—CH($(CH_2)_n$NH—$R^4$)—C(O) or is deleted;
$A^{21}$ is Val, Leu, Ile, Phe, Nle, β-Nal, Aib, p-X-Phe, Acc, Cha, Met or is deleted;
$A^{22}$ is Acc, Aib, Glu or is deleted;
$A^{23}$ is Trp, Acc, Phe, p-X-Phe, Aib, β-Nal or Cha;
$A^{24}$ is Leu, Acc, Ile, Val, Phe, β-Nal, Nle, Aib, p-X-Phe or Cha;
$A^{25}$ is Arg, Lys or HN—CH($(CH_2)_n$NH—$R^4$)—C(O);
$A^{26}$ is Arg, Lys or HN—CH($(CH_2)_n$NH—$R^4$)—C(O);
$A^{27}$ is Lys, Aib, Leu, hArg, Gln, Acc, Arg, Cha, Nle, Ile, Val, Phe, β-Nal, or p-X-Phe, where the Lys is optionally substituted on the ε-amino group by an acyl group;
$A^{28}$ is Leu, Acc, Cha, Ile, Val, Phe, Nle, β-Nal, Aib or p-X-Phe;
$A^{29}$ is Gln, Acc or Aib;
$A^{30}$ is Asp, Lys, Arg or is deleted;
$A^{31}$ is Val, Leu, Nle, Acc, Cha, Phe, Ile, β-Nal, Aib, p-X-Phe or is deleted;
$A^{32}$ is His or is deleted;
$A^{33}$ is Asn or is deleted;
$A^{34}$ is Phe, Tyr, Amp, Aib, β-Nal, Cha, Nle, Leu, Ile, Acc, p-X-Phe or is deleted;
$A^{35}$ is Val, Leu, Nle, Acc, Cha, Phe, Ile, β-Nal Aib, p-X-Phe or is deleted;
$A^{36}$ is Ala, Val, Aib, Acc, Nva, Abu or is deleted;
$A^{37}$ is Leu, Val, Nle, Ile, Cha, β-Nal, Trp, Pal, Acc, Phe, p-X-Phe, a lipophilic amino acid, or is deleted;
$A^{38}$ is Gly, Acc, Aib, or is deleted;
where X for each occurrence is independently selected from the group consisting of OH, a halo and $CH_3$;
$R^1$ and $R^2$ are each independently selected from the group consisting of H, $(C_1$-$C_{30})$alkyl, $(C_2$-$C_{30})$alkenyl, phenyl-$(C_1$-$C_{30})$alkyl, naphthyl$(C_1$-$C_{30})$alkyl, hydroxy$(C_1$-$C_{30})$alkyl, hydroxy$(C_2$-$C_{30})$alkenyl, hydroxy-phenyl$(C_1$-$C_{30})$alkyl or hydroxy-naphthyl $(C_1$-$C_{30})$alkyl;
or one of $R^1$ or $R^2$ is $COE^1$ where $E^1$ is $(C_1$-$C_{30})$alkyl, $(C_2$-$C_{30})$alkenyl, phenyl$(C_1$-$C_{30})$alkyl, naphthyl$(C_1$-$C_{30})$alkyl, hydroxy$(C_1$-$C_{30})$alkyl, hydroxy$(C_2$-$C_{30})$alkenyl, hydroxy-phenyl$(C_1$-$C_{30})$alkyl or hydroxy-naphthyl$(C_1$-$C_{30})$alkyl;
$R^3$ is OH, $NH_2$, $(C_1$-$C_{30})$alkoxy or NH-Y-$CH_2$-Z, where Y is a $(C_1$-$C_{30})$ hydrocarbon moiety and Z is $CO_2H$ or $CONH_2$;
n for each occurrence is independently an integer from 1 to 5; and
$R^4$ for each occurrence is independently $(C_1$-$C_{30})$alkyl, $(C_1$-$C_{30})$acyl or —C((NH)($NH_2$));

provided that when $A^8$ is not a lipophilic D-amino acid or is not deleted then at least one of $A^6$, $A^7$, $A^9$, $A^{10}$, $A^{11}$ and $A^{12}$ is a D-amino acid or at least one of $A^6$, $A^7$, $A^9$, $A^{10}$, $A^{11}$, $A^{12}$, $A^{13}$, $A^{14}$, $A^{15}$, $A^{16}$, $A^{17}$, $A^{18}$, $A^{19}$, $A^{20}$, $A^{21}$ and $A^{22}$ is deleted; and further provided that when the compound contains a D-amino acid then $A^{36}$ is deleted.

A preferred group of compounds of formula (III) are the compounds listed as Examples 1-73, shown hereinbelow. Of the compounds listed as Examples 1-73, the following compounds are preferred: [Cha⁷,¹¹, des-Met⁸, Nle¹⁸, Tyr³⁴]hPTH-(1-34)$NH_2$ (SEQ ID NO:16), [Cha⁷,¹¹, D-Nle⁸, des-Met¹⁸, Tyr³⁴]hPTH-(1-34)$NH_2$, [Cha⁷,¹¹, D-Nle⁸, Nle¹⁸, Tyr³⁴]hPTH-(1-34)$NH_2$, [D-Nle⁸, Nle¹⁸, Tyr³⁴]hPTH(1-34)$NH_2$ and [D-Bpa⁸, Tyr³⁴]hPTH(1-34)$NH_2$.

In yet another aspect, this invention provides a compound of formula (V), $(R^1R^2)$-$A^1$-$A^2$-$A^3$-$A^4$-$A^5$-$A^6$-$A^7$-$A^8$-$A^9$-$A^{10}$-$A^{11}$-$A^{12}$-$A^{13}$-$A^{14}$-$A^{15}$-$A^{16}$-$A^{17}$-$A^{18}$-$A^{19}$-$A^{20}$-$A^{21}$-$A^{22}$-$A^{23}$-$A^{24}$-$A^{25}$-$A^{26}$-$A^{27}$-$A^{28}$-$A^{29}$-$A^{30}$-$A^{31}$-$A^{32}$-$A^{33}$-$A^{34}$-$A^{35}$-$A^{36}$-$A^{37}$-$A^{38}$-$R^3$, (V)

or a pharmaceutically acceptable salt thereof, wherein
$A^1$ is Ala, Ser, Dap, Thr, Aib or is deleted;
$A^2$ is Val or is deleted;
$A^3$ is Ser, Aib, Thr or is deleted;
$A^4$ is Glu, Asp or is deleted;
$A^5$ is His, Ile, Acc, Val, Nle, Phe, Leu, p-X-Phe, β-Nal, Aib, Cha or is deleted;
$A^6$ is Gln, a hydrophilic amino acid or is deleted;

$A^7$ is Leu, Val, Cha, Nle, β-Nal, Trp, Pal, Acc, Phe, p-X-Phe, Aib, a lipophilic amino acid or is deleted;

$A^8$ is Leu, Met, Acc, Cha, Aib, Nle, Phe, Ile, Val, β-Nal, p-X-Phe, a lipophilic amino acid or is deleted;

$A^9$ is His, a hydrophilic amino acid or is deleted;

$A^{10}$ is Asp, Asn, a hydrophilic amino acid or is deleted;

$A^{11}$ is Lys, Arg, Leu, Cha, Aib, p-X-Phe, Ile, Val, Nle, Acc, Phe, β-Nal, HN—CH(($CH_2)_n$NH—$R^4$)—C(O), a lipophilic D-amino acid, a hydrophilic amino acid or is deleted;

$A^{12}$ is Gly, Acc, Aib, or is deleted;

$A^{13}$ is Lys, Arg, HN—CH(($CH_2)_n$NH—$R^4$)—C(O) or is deleted;

$A^{14}$ is Ser, His or is deleted;

$A^{15}$ is Ile, Acc, Cha, Leu, Phe, Nle, β-Nal, Trp, p-X-Phe, Val, Aib or is deleted;

$A^{16}$ is Gln, Aib or is deleted;

$A^{17}$ is Asp, Aib or is deleted;

$A^{18}$ is Leu, Aib, Acc, Cha, Phe, Ile, Nle, β-Nal, Val, p-X-Phe or is deleted;

$A^{19}$ is Arg, Lys, Aib, HN—CH(($CH_2)_n$NH—$R^4$)—C(O) or is deleted;

$A^{20}$ is Arg, Lys, HN—CH(($CH_2)_n$NH—$R^4$)—C(O) or is deleted;

$A^{21}$ is Arg, Lys, HN—CH(($CH_2)_n$NH—$R^4$)—C(O) or is deleted;

$A^{22}$ is Phe, Glu, Aib, Acc, p-X-Phe, β-Nal, Val, Leu, Ile, Nle or Cha;

$A^{23}$ is Phe, Leu, Lys, Acc, Cha, β-Nal, Aib, Nle, Ile, p-X-Phe, Val or Trp;

$A^{24}$ is Leu, Lys, Acc, Nle, Ile, Val, Phe, β-Nal, Aib, p-X-Phe, Arg or Cha;

$A^{25}$ is His, Lys, Aib, Acc, Arg or Glu;

$A^{26}$ is His, Aib, Acc, Arg or Lys;

$A^{27}$ is Leu, Lys, Acc, Arg, Ile, Val, Phe, Aib, Nle, β-Nal, p-X-Phe or Cha;

$A^{28}$ is Ile, Leu, Lys, Acc, Cha, Val, Phe, p-X-Phe, Nle, β-Nal, Aib or is deleted;

$A^{29}$ is Ala, Glu, Acc, Aib or is deleted;

$A^{30}$ is Glu, Leu, Nle, Cha, Aib, Acc, Lys, Arg or is deleted;

$A^{31}$ is Ile, Leu, Cha, Lys, Acc, Phe, Val, Nle, β-Nal, Arg or is deleted;

$A^{32}$ is His or is deleted;

$A^{33}$ is Thr, Ser or is deleted;

$A^{34}$ is Ala, Phe, Tyr, Cha, Val, Ile, Leu, Nle, β-Nal, Aib, Acc or is deleted;

$A^{35}$ is Glu, Asp or is deleted;

$A^{36}$ is Ile, Acc, Cha, Leu, Phe, Nle, β-Nal, Trp, p-X-Phe, Val, Aib or is deleted;

$A^{37}$ is Arg, Lys, HN—CH(($CH_2)_n$NH—$R^4$)—C(O) or is deleted;

$A^{38}$ is Ala, Phe, Tyr, Cha, Val, Ile, Leu, Nle, β-Nal, Aib, Acc or is deleted;

$R^1$ and $R^2$ are each independently selected from the group consisting of H, ($C_1$-$C_{30}$)alkyl, ($C_2$-$C_{30}$)alkenyl, phenyl-($C_1$-$C_{30}$)alkyl, naphthyl($C_1$-$C_{30}$)alkyl, hydroxy($C_1$-$C_{30}$)alkyl, hydroxy($C_2$-$C_{30}$)alkenyl, hydroxy-phenyl($C_1$-$C_{30}$)alkyl or hydroxy-naphthyl($C_1$-$C_{30}$)alkyl;

or one of $R^1$ or $R^2$ is $COE^1$ where $E^1$ is ($C_1$-$C_{30}$)alkyl, ($C_2$-$C_{30}$)alkenyl, phenyl($C_1$-$C_{30}$)alkyl, naphthyl($C_1$-$C_{30}$)alkyl, hydroxy($C_1$-$C_{30}$)alkyl, hydroxy($C_2$-$C_{30}$)alkenyl, hydroxy-phenyl($C_1$-$C_{30}$)alkyl or hydroxy-naphthyl($C_1$-$C_{30}$)alkyl;

$R^3$ is OH, $NH_2$, ($C_1$-$C_{30}$)alkoxy or NH-Y-$CH_2$-Z, where Y is a ($C_1$-$C_{30}$) hydrocarbon moiety and Z is $CO_2H$ or $CONH_2$;

n for each occurrence is independently an integer from 1 to 5; and $R^4$ for each occurrence is independently ($C_1$-$C_{30}$)alkyl, ($C_1$-$C_{30}$)acyl or —C((NH)($NH_2$));

provided that when $A^8$ is not a lipophilic D-amino acid or is not deleted then at least one of $A^6, A^7, A^9, A^{10}, A^{11}$ and $A^{12}$ is a D-amino acid or at least one of $A^6, A^7, A^9, A^{10}, A^{11}, A^{12}, A^{13}, A^{14}, A^{15}, A^{16}, A^{17}, A^{18}, A^{19}, A^{20}, A^{21}$ and $A^{22}$ is deleted.

A preferred group of compounds of formula (V) are the compounds listed as Examples 74-86, shown hereinbelow.

In a further aspect, this invention provides a method of selectively binding the PTH2 receptor which comprises administering to a patient in need thereof an analogue of formula (I), (II) or (III) or a pharmaceutically acceptable salt thereof.

In another aspect, this invention provides a method of selectively binding the PTH2 receptor which comprises administering to a patient in need thereof a compound of formula (III) or (V) or a pharmaceutically acceptable salt thereof. Preferred of the foregoing method is where the compound is selected from Examples 1-73 or Examples 74-86.

In another aspect, this invention is directed to a pharmaceutical composition comprising an analogue of formula (I), (II) or (III) or a pharmaceutically acceptable salt thereof and a pharmaceutically acceptable carrier.

In still another aspect, this invention is directed to a pharmaceutical composition comprising a compound of formula (III) or (V) or a pharmaceutically acceptable salt thereof and a pharmaceutically acceptable carrier. Preferred is a pharmaceutical composition comprising a compound selected from Examples 1-73 or Examples 74-86.

In still another aspect, this invention is directed to a method of treating a medical disorder that results from altered or excessive action of the PTH2 receptor, which comprises administering to a patient in need thereof an effective amount of a PTH analogue or a truncated PTH analogue or a pharmaceutically acceptable salt thereof that selectively binds to the PTH2 receptor, sufficient to inhibit the activation of the PTH2 receptor of said patient. A preferred method of the immediately foregoing method is where said medical disorder is abnormal CNS functions, abnormal pancreatic functions, divergence from normal mineral metabolism and homeostasis, male infertility, abnormal blood pressure or a hypothalmic disease. Preferred of each of the immediately foregoing methods is where the analogue is a PTH2 agonist or a PTH2 antagonist.

In another aspect, this invention provides a method of treating a medical disorder that results from altered or excessive action of the PTH2 receptor, which comprises administering to a patient in need thereof an effective amount of an analogue of formula (I), (II) or (III), sufficient to inhibit the activation of the PTH2 receptor of said patient. A preferred method of the immediately foregoing method is where said medical disorder is abnormal CNS functions, abnormal pancreatic functions, divergence from normal mineral metabolism and homeostasis, male infertility, abnormal blood pressure or a hypothalmic disease.

In another aspect, this invention is directed to a method of treating a medical disorder that results from altered or excessive action of the PTH2 receptor, which comprises administering to a patient in need thereof an effective amount of a compound of formula (III) or (V), sufficient to inhibit the activation of the PTH2 receptor of said patient. A preferred method of the immediately foregoing method is where said medical disorder is abnormal CNS functions, abnormal pancreatic functions, divergence from normal mineral metabolism and homeostasis, male infertility, abnormal blood pressure or a hypothalmic disease. Preferred of each of the foregoing methods is where the compound is selected from Examples 1-73 or Examples 74-86.

DETAILED DESCRIPTION

With the exception of the N-terminal amino acid, all abbreviations (e.g. Ala or $A_1$) of amino acids in this disclosure stand for the structure of —NH—CH(R)—CO—, wherein R is the side chain of an amino acid (e.g., $CH_3$ for Ala). For the N-terminal amino acid, the abbreviation stands for the structure of $(R^1R^2)$—N—CH(R)—CO—, wherein R is a side chain of an amino acid and $R^1$ and $R^2$ are as defined above. Bpa is p-benzoylphenylalanine. β-Nal, Nle, Dap, Cha, Nva, Amp, Pal, and Aib are the abbreviation of the following α-amino acids: β-(2-naphthyl)alanine, norleucine, α,β-diaminopropionic acid, cyclohexylalanine, norvaline, 4-amino-phenylalanine, β-(3-pyridinyl)alanine and α-aminoisobutyric acid, respectively. What is meant by Acc is an amino acid selected from the group of 1-amino-1-cyclopropanecarboxylic acid; 1-amino-1-cyclobutanecarboxylic acid; 1-amino-1-cyclopentanecarboxylic acid; 1-amino-1-cyclohexanecarboxylic acid; 1-amino-1-cycloheptanecarboxylic acid; 1-amino-1-cyclooctanecarboxylic acid; and 1-amino-1-cyclononanecarboxylic acid. In the above formula hydroxyalkyl, hydroxyphenylalkyl, and hydroxynaphthylalkyl may contain 1-4 hydroxy substituents. $COE_1$ stands for —C=O.$E^1$. Examples of —C=O.$E^1$ include, but are not limited to, acetyl and phenylpropionyl. What is meant by "$(C_{1-12})$ hydrocarbon moiety" is an alkyl group, an alkenyl group or an alkynyl group.

What is meant by a "hydrophilic amino acid" is an amino acid having at least one hydrophilic functional group in addition to those required for peptide bond formation, such as: Arg, Asp, Asn, Glu, Gln, Gly, His, Lys, Orn (ornithine), Ser, Thr, β-Ala, Ala, Aad (α-aminoadipic acid), β-Aad (β-aminoadipic acid), Apm (α-aminopimolic acid), Cit (citrulline), Gla (γ-carboxy-glutamic acid), hArg (homo-Arg), hCit (homo-Cit), hSer (homo-Ser), Dba (α,γ-diamino-butyric acid), Dpa (α,β-diaminopropionic acid), Amp (p-amino-phenylalanine), Pal, and their homologues.

What is meant by a "lipophilic amino acid" is an uncharged, aliphatic or aromatic amino acid, such as: Val, Leu, Ile, Pro, Cys, Phe, Met, Trp, Tyr, Cha, β-Nal, Aib, Acc, Ala, Abu (α-aminobutyric acid), Nle, Nva (norvaline), Bpa (p-benzoyl-phenylalanine), hPhe (homo-Phe), hPro (homo-Pro), 1-Nal (β-(1-naphthyl)alanine), 2-Nal (β(2-naphthyl) alanine), Oic (octahydroindode-2-carboxylic acid), Tic (1,2, 3,4-tetrahydroisoquinoline-3-carboxylic acid), Pen (penicillamine), Phg (phenylglycine), Tle (t-leucine), p-X-Phe (X=Br, F, I, Cl, CH, phenyl, CN, $NO_2$), Tal (β-(2-thienyl)-alanine), and their homologues.

Alanine, β-alanine and sarcosine (Sar) may be considered either a hydrophilic or a lipophilic amino acid.

"Physiologically active truncated homologue or analogue of PTH" refers to a polypeptide having a sequence comprising less than the full complement of amino acids found in PTH.

The full names for other abbreviations used herein are as follows: Boc for t-butyloxycarbonyl, HF for hydrogen fluoride, Fm for formyl, Xan for xanthyl, Bzl for benzyl, Tos for tosyl, DNP for 2,4-dinitrophenyl, DMF for dimethylformamide, DCM for dichloromethane, HBTU for 2-(1H-Benzotriazol-1-yl)-1,1,3,3-tetramethyl uronium hexafluorophosphate, DIEA for diisopropylethylamine, HOAc for acetic acid, TFA for trifluoroacetic acid, 2ClZ for 2-chlorobenzyloxycarbonyl and OcHex for O-cyclohexyl.

A peptide of this invention is also denoted herein by another format, e.g., [D-$Nle^8$]hPTH(1-34)$NH_2$, with the substituted amino acids from the natural sequence placed between the set of brackets (e.g., D-$Nle^8$ for $Met^8$ in hPTH). The abbreviation hPTH stands for human PTH, for hPTHrP for human PTHrP. The numbers between the parantheses refer to the number of amino acids present in the peptide (e.g., hPTH(1-34) is amino acids 1 through 34 of the peptide sequence for human PTH; SEQ ID NO:1). The sequences for hPTH(1-34) (SEQ ID NO:1) and hPTHrP(1-34) (SEQ ID NO:2) are listed in Nissenson, et al., Receptor, 3:193 (1993). The designation "$NH_2$" in PTH(1-34)$NH_2$ (SEQ ID NO:53) indicates that the C-terminus of the peptide is amidated. PTH (1-34) (SEQ ID NO:1) means that the C-terminus is the free acid.

The peptides of this invention can be prepared by standard solid phase peptide synthesis. See, e.g., Stewart, J. M., et al., Solid Phase Synthesis (Pierce Chemical Co., 2d ed. 1984). The substituents $R^1$ and $R^2$ of the above generic formula may be attached to the free amine of the N-terminal amino acid by standard methods known in the art. For example, alkyl groups, e.g., $(C_{1-12})$alkyl, may be attached using reductive alkylation. Hydroxyalkyl groups, e.g., $(C_{1-12})$hydroxyalkyl, may also be attached using reductive alkylation wherein the free hydroxy group is protected with a t-butyl ester. Acyl groups, e.g., $COE^1$, may be attached by coupling the free acid, e.g., $E^1$COOH, to the free amine of the N-terminal amino acid by mixing the completed resin with 3 molar equivalents of both the free acid and diisopropylcarbodiimide in methylene chloride for one hour. If the free acid contains a free hydroxy group, e.g., p-hydroxyphenylpropionic acid, then the coupling should be performed with an additional 3 molar equivalents of HOBT.

When $R^3$ is NH-Y-$CH_2$—$CONH_2$ (Z=$CONH_2$), the synthesis of the peptide starts with BocNH-Y-$CH_2$—COOH which is coupled to the resin. If $R^3$ is NH-Y-$CH_2$—COOH (Z=COOH) the synthesis of the peptide starts with Boc-HN-Y-$CH_2$—COOH which is coupled to PAM resin. When $R^3$ is OH the first amino acid is coupled to PAM resin.

The compounds of this invention can be tested for binding to the human PTH2 (hPTH2) receptor for the ability to stimulate adenylyl cyclase and/or intracellular calcium transients by the assay described below.

Materials and Methods: Tissue culture media and sera were purchased from Life Technologies (Grand Island, N.Y.), and all tissue culture plastics were obtained from Corning (Corning, N.Y.). Adenosine and 3-isobutyl-1-methyl xanthine (IBMX) were purchased from Research Biochemicals (Natick, Mass.). Fura-2 acetoxylmethyl ester (fura-2/AM) was obtained from Molecular Probes (Eugene, Oreg.), and hPTHrP was purchased from Bachem (Torrance, Calif.). [$^3$H]-Adenine was purchased from New England Nuclear (Boston, Mass.). $Na^{125}I$ was obtained from Amersham Corp. (Arlington Heights, Ill.). All other analytical grade reagents were purchased from Sigma (St. Louis, Mo.).

Cell Culture: Human osteosarcoma Saos-2/B-10 cells (American Type Culture Collection, Rockville, Md.; ATCC #HTB 85) are maintained in RPMI 1640 medium (Sigma, St. Louis, Mo.) supplemented with 10% fetal bovine serum (FBS) and 2 mM glutamine at 37° C. in a humidified atmosphere of 5% $CO_2$ in air. The medium is changed every three or four days, and the cells are subcultured every week by trypsinization. Stably transfected HEK-293/BP-16 cells (Beth Israel Deaconess Medical Center-Division of Bone and Mineral Metabolism, Boston, Mass.), which express the hPTH2 receptor (160,000 receptors/cell) and stably transfected HEK-293/C-21 cells (Beth Israel Deaconess Medical Center-Division of Bone and Mineral Metabolism, Boston, Mass.), which express the hPTH/PTHrP receptor, are maintained in DMEM supplemented with 10% FBS at 37° C. in a humidified atmosphere of 95% air/5% $CO_2$. The medium is changed every 2 days before confluency and every day after confluency. The cells are sub-cultured 1:10 once a week.

Receptor binding assay: Ligand binding is performed using Saos-2/B-10, HEK/C-21 cells or HEK/BP-16 cells using HPLC-purified [$^{125}$I][Hle$^{8,18}$, Tyr$^{34}$]bPTH-(1-34)NH$_2$ ($^{125}$I-PTH) (SEQ ID NO:17) as radioligand. Saos-2 cells are maintained for four days until they reach confluence. The medium is replaced with 5% FBS in RPMI 1640 medium and incubated for about 2 hours at room temperature with 10×10$^4$ cpm mono-$^{125}$I-[Nle$^{8,18}$, Tyr$^{34}$(3-$^{125}$I)bPTH(1-34)NH$_2$ (SEQ ID NO:17) in the presence of competing peptides of the invention at various concentrations between 10$^{-11}$M to 10$^{-4}$M. The cells are washed four times with ice-cold PBS and lysed with 0.1 M NaOH, and the radioactivity associated with the cells is counted in a scintillation counter. Synthesis of mono-$^{125}$I-[Nle$^{8,18}$, Tyr$^{34}$(3-$^{125}$I)bPTH(1-34)NH$_2$ (SEQ ID NO:17) is carried out as described in Goldman, M. E., et al., Endocrinol., 123:1468 (1988).

The binding assay is conducted with various peptides of the invention, and the Kd value (half maximal inhibition of binding of mono-$^{125}$I-[Nle$^{8,18}$, Tyr$^{34}$(3-$^{125}$I)bPTH(1-34)NH$_2$ (SEQ ID NO:17)) for each peptide is calculated.

Adenylyl cyclase assay: Adenylyl cyclase assay is performed in Saos-2/B-10 cells, HEK/C21 cells, and HEK/BP-16 cells. The ability of the peptides of the invention to induce a biological response in Saos-2/B-10 cells is measured. More specifically, any stimulation of the adenylate cyclase is determined by measuring the level of synthesis of cAMP (adenosine 3',5'-monophosphate) as described previously in Rodan, et al., J. Clin. Invest. 72: 1511 (1983) and Goldman, et al., Endocrinol., 123:1468 (1988). Confluent Saos-2/B-10 cells in 24 well plates at 4×10$^4$ cells/well in RPMI1640 medium containing 10% FBS. Cells are washed twice with $Ca^{2+}$ and $Mg^{2+}$ free Hanks' balanced salt solution and incubated with 0.5 µCi [$^3$H]adenine (26.9 Ci/mmol, New England Nuclear, Boston, Mass.) in fresh medium at about 37° C. for about 2 hrs, and washed twice with Hank's balanced salt solution (Gibco, Gaithersburg, Md.). The cells are treated with 1 mM IBMX [isobutylmethyl-xanthine, Sigma, St. Louis, Mo.] in fresh medium for 15 min, and a peptide to be tested is added to the medium to incubate for about 5 min. The reaction is stopped by the addition of 1.2 M trichloroacetic acid (TCA) (Sigma, St. Louis, Mo.) followed by sample neutralization with 4 N KOH. cAMP is isolated by the two-column chromatographic method (Salmon, et al., 1874, Anal. Biochem. 58, 541). The radioactivity is counted in a scintillation counter (Liquid Scintillation Counter 2200CA, PACKARD, Downers Grove, Ill.).

Measurements of $[Ca^{2+}]_i$: Measurements of intracellular $Ca^{2+}$ ($[Ca^{2+}]$) are performed in Saos-2/B-10 cells, HEK/C-21 cells and HEK/BP-16 cells. For measurement of $[Ca^{2+}]_i$, cells are harvested from 150-cm$^2$ flasks using HEPES-buffered balanced salt solution containing 0.02% (vol/vol) EDTA. The cell suspension is washed three times with Hanks' Balanced Salt Solution (1 mM $CaCl_2$, 118 mM NaCl, 4.6 mM KCl, 10 mM d-glucose, and 20 mM HEPES, pH 7.4), and cells are loaded with fura-2/AM (1 µM) for about 40 min at about 37° C. The cell suspension is washed three times with Hanks' Balanced Salt Solution, and fluorescence is measured in a SPEX AR-CM system spectrofluorimeter (SPEX Industries, Edison, N.J.). Dual wavelength measurements are performed (excitation wavelengths, 340 and 380 nm; emission wavelength, 505 nm).

$[Ca^{2+}]_i$ is calculated from fura-2 ratios (R) by the equation: $[Ca^{2+}]_i = K(R - R_{min})/(R_{max} - R)$, where $R_{min}$ and $R_{max}$ are the ratios (e.g. 340 nm/380 nm) for the minimal or maximal calcium concentration, respectively. K is the product $K_d(F_O/F_S)$, where $K_d$ is the effective dissociation constant (224 nM), $F_O$ is the intensity of the 380-nm excitation signal in the absence of calcium, and $F_S$ is the intensity of the 380-nm excitation signal at saturating calcium concentrations. Maximum fluorescence intensity is obtained by permeabilizing the cells with 50 µM digitonin in the presence of 1 mM $CaCl_2$, and minimal fluorescence intensity is obtained by chelating calcium with 16.6 mM EGTA [pH adjusted to 8.3 with 3M Tris-(hydroxymethyl)aminomethane base]. Addition of vehicle alone (0.1% BSA in PBS) did not change the level of $[Ca^{2+}]_i$.

The peptides of this invention can be provided in the form of pharmaceutically acceptable salts. Examples of such salts include, but are not limited to, those formed with organic acids (e.g., acetic, lactic, maleic, citric, malic, ascorbic, succinic, benzoic, methanesulfonic, toluenesulfonic or pamoic acid), inorganic acids (e.g., hydrochloric acid, sulfuric acid, or phosphoric acid), and polymeric acids (e.g., tannic acid, carboxymethyl cellulose, polylactic, polyglycolic, or copolymers of polylactic-glycolic acids).

A therapeutically effective amount of a peptide of this invention and a pharmaceutically acceptable carrier substance (e.g., magnesium carbonate, lactose, or a phospholipid with which the therapeutic compound can form a micelle) together form a therapeutic composition (e.g., a pill, tablet, capsule, or liquid) for administration (e.g., orally, intravenously, transdermally, pulmonarily, vaginally, subcutaneously, nasally, iontophoretically, or by intratracheally) to a subject. The pill, tablet or capsule that is to be administered orally can be coated with a substance for protecting the active composition from the gastric acid or intestinal enzymes in the stomach for a period of time sufficient to allow it to pass undigested into the small intestine. The therapeutic composition can also be in the form of a biodegradable or nonbiodegradable sustained release formulation for subcutaneous or intramuscular administration. See, e.g., U.S. Pat. Nos. 3,773,919 and 4,767,628 and PCT Application No. WO 94/15587. Continuous administration can also be achieved using an implantable or external pump (e.g., INFUSAID™ pump). The administration can also be conducted intermittently, e.g., single daily injection, or continuously at a low dose, e.g., sustained release formulation.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions.

They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as coca butter or a suppository wax.

Compositions for nasal or sublingual administration are also prepared with standard excipients well known in the art.

Further, a compound of this invention can be administered in a sustained release composition such as those described in the following patents. U.S. Pat. No. 5,672,659 teaches sustained release compositions comprising a bioactive agent and a polyester. U.S. Pat. No. 5,595,760 teaches sustained release compositions comprising a bioactive agent in a gelable form. U.S. application No. 08/929,363 filed Sep. 9, 1997, teaches polymeric sustained release compositions comprising a bioactive agent and chitosan. U.S. application No. 08/740,778 filed Nov. 1, 1996, teaches sustained release compositions comprising a bioactive agent and cyclodextrin. U.S. application No. 09/015,394 filed Jan. 29, 1998, teaches absorbable sustained release compositions of a bioactive agent. The teachings of the foregoing patents and applications are incorporated herein by reference.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. Generally, dosage levels of between 0.0001 to 10 mg/kg of body weight daily are administered.

A preferred dosage range is 0.001 to 0.5 mg/kg of body weight daily which can be administered as a single dose or divided into multiple doses.

The compounds of the instant invention are illustrated by the following examples, but are not limited to the details thereof.

EXAMPLE 1

[Cha$^{7,11}$, D-Nle$^8$, Nle$^{18}$, Tyr$^{34}$]hPTH(1-34)NH$_2$

The peptide [Cha$^{7,11}$, D-Nle$^8$, Nle$^{18}$, Tyr$^{34}$]hPTH(1-34)NH$_2$ was synthesized on an Applied Biosystems (Foster City, Calif.) model 430A peptide synthesizer which was modified to do accelerated Boc-chemistry solid phase peptide synthesis. See Schnoize, et al., Int. J. Peptide Protein Res., 90:180 (1992). 4-Methylbenzhydrylamine (MBHA) resin (Peninsula, Belmont, Calif.) with the substitution of 0.93 mmol/g was used. The Boc amino acids (Bachem, Calif., Torrance, Calif.; Nova Biochem., LaJolla, Calif.) were used with the following side chain protection: Boc-Asn(Xanthyl), Boc-Arg(Tos)-OH, Boc-Asp(OcHex)-OH, Boc-Glu(OcHex)-OH, Boc-His(DNP)-OH, Boc-Cha-OH, Boc-D-Nle-OH, Boc-Nle-OH, Boc-Val-OH, Boc-Leu-OH, Boc-Gly-OH, Boc-Gln-OH, Boc-Ile-OH, Boc-Lys(2ClZ)-OH, Boc-Ser(Bzl)-OH; Boc-Trp(formyl)-OH and Boc-Tyr(Br-Z)-OH (where Z is benzyloxycarbonyl). The synthesis was carried out on a 0.14 mmol scale. The Boc groups were removed by treatment with 100% TFA for 2×1 min. Boc amino acids (2.5 mmol) were pre-activated with HBTU (2.0 mmol) and DIEA (1.0 mL) in 4 mL of DMF and were coupled without prior neutralization of the peptide-resin TFA salt. Coupling times were about 5 min.

At the end of the assembly of the peptide chain, the resin was treated with a solution of 20% mecaptoethanol/10% DIEA in DMF for 2×30 min. to remove the DNP group on the His side chain. The resin was washed with DMF. The N-terminal Boc group was then removed by treatment with 100% TFA for 2×2 min. The resin was washed with DMF and was treated with ethanolamine:H$_2$O:DMF/15:15:70 for 2×30 min. to remove the formyl protecting group on Trp residue. The partially-deprotected peptide-resin was washed with DMF and DCM and dried in vacuo. The final cleavage was done by stirring the peptide-resin in 10 mL of HF containing 1 mL of anisole and dithiothreitol (24 mg) at about 0° C. for about 75 min. HF was removed by a flow of nitrogen. The residue was washed with ether (6×10 mL) and extracted with 4N HOAc (6×10 mL).

The peptide mixture in the aqueous extract was purified on a reverse-phase preparative high pressure liquid chromatography (HPLC) using a reverse phase VYDAC™ C$_{18}$ column (Nest Group, Southborough, Mass.). The column was eluted with a linear gradient (10% to 45% of solution B in solution A over 130 min.) at a flow rate of 10 mL/min (Solution A=water containing 0.1% TFA; Solution B=acetonitrile containing 0.1% of TFA). Fractions were collected and checked on analytical HPLC. Those containing pure product were combined and lyophilized to dryness. 114 mg of a white solid was obtained. Purity was >98% based on analytical HPLC analysis. Electro-spray mass spectrometer analysis gave the molecular weight at 4176.4 (in agreement with the calculated molecular weight of 4176.9).

EXAMPLE 2

[D-Nle$^8$, Nle$^{18}$, Tyr$^{34}$]hPTH(1-34)NH$_2$

Boc-protected amino acids, N-hydroxybenzotriazole (HOBt), N,N'-dicyclohexylcarbodilmide (DCC) and p-methylbenzhydrylamine resin were purchased from Applied Biosystems (Foster City, Calif.). Boc-(3-Iodo)Tyrosine[O-(3-BrBz)] was purchased from Peninsula Laboratories (Belmont, CA). B&J brand dichloromethane, N-methylpyrrolidone (NMP) and acetonitrile were obtained from Baxter (McGraw Park, Ill.). All other reagents are commercially available, for example from Sigma (St. Louis, Mo.). The title peptide was synthesized by solid-phase Boc/HOBt/NMP chemistry on an automated Applied Biosystems 430A peptide synthesizer using software version 1.40. The following side-chain protected N-α-Boc-amino derivatives were used in the course of the automated solid-phase peptide synthesis: Arg(N$^G$-tosyl), Asp(O-cHex), Glu(O-Bzl), His(N$^\pi$-Bom), Lys(N$^\epsilon$-2-Cl-Z), Ser(O-Bzl), Thr(O-Bzl), and Tyr(2-Br-Z). Synthesis started at a 0.5 mmol scale and was split into two halves after the incorporation of Glu$^{22}$. The following residues were incorporated by double coupling cycles: Arg$^{25}$, Leu$^{24}$, Val$^{21}$, Arg$^{20}$, Glu$^{19}$, Leu$^{15}$, His$^{14}$, Lys$^{13}$, His$^9$, Phe$^7$, Gln$^6$ and Ile$^5$. The Nle in positions 18 and 8 was introduced in the form of pre-dissolved NMP solution and the Activator cycle was modified accordingly. Cleavage of the peptide from the ρMBHA resin utilized liquid hydrogen fluoride and followed the "Low-High" procedure. The "Low-HF" step included mixing the suspension of the resin-bound peptide in a mixture (20 mL/g of resin-bound peptide) containing (% vol) 60% dimethylsulfide, 5% ρ-thiocresol, 5% ρ-cresol, 5% ethane dithiol, and 25% HF for about 2 hours at about 0° C. After removal of the volatile reagent under vacuum and washing the resin-bound peptide consecutively with petroleum-ether and ether it was returned to the reaction vessel for the "High-HF" step. The resin-bound peptide was resuspended in a mixture (20 mL/g or resin-bound peptide) containing (% vol) 5% butane dithiol, 5% ρ-cresol, and 90% HF for about 1 hour at about 0° C. After removing the reagents as previously described the crude peptide was dissolved in 50% (v/v) acetic acid and the solution was diluted with water and lyophilized. The peptide was purified by preparative reverse-phase high performance liquid chromatography (RP-HPLC) (PrepPak VYDAC® C18, 300Å cartridge, 15 μm, 5.5×35 cm). The solvent system employed included a two solvent system: A: 0.1% (v/v) TFA in water and B: 0.1% (v/v) TFA in acetonitrile, generating the following linear gradient: 0-15% B in A in the first 10 min followed by 15-45% B in A in the next 120 min at a flow-rate of 70 mL/min and monitored at 220 nm. Fractions were analyzed on an analytical RP-HPLC system (VYDAC® (C18, 300Å, 5 μm, 4.6×150 cm) employing a linear gradient of 20-50% B in A for 30 min at a flow rate of 1 ml/min and monitored at 220 nm, the retention time is 18.24 minutes. The pure fractions were pooled and the acetonitrile removed under vacuum. The residual was lyophilized to yield a white powder. Purity and structure of the peptides were confirmed by analytical RP-HPLC, amino acid analysis, and Fast Atom Bombardment Mass Spectrometry, mass spec.=4097.0.

EXAMPLES 3-5

Examples 3-4 were synthesized substantially according to the procedure of Example 1 using the appropriate, protected amino acids and Example 5 was synthesized substantially according to Example 2 using the appropriate, protected amino acids.

| Example | Name | Mass Spec. |
|---|---|---|
| 3 | [Cha$^{7,11}$, des-Met$^8$, Nle$^{18}$, Tyr$^{34}$]hPTH(1-34)NH$_2$ (SEQ ID NO:16) | 4063.5 |
| 4 | [Cha$^{7,11}$, D-Nle$^8$, des-Met$^{18}$, Tyr$^{34}$]hPTH(1-34)NH$_2$ | 4063.4 |
| 5 | [D-Bpa$^8$, Tyr$^{34}$]hPTH-(1-34)NH$_2$ | 4320.7 |

EXAMPLES 6-86

Examples 6 to 86 can be synthesized substantially according to the procedure of Example 1 using the appropriate, protected amino acids.

Example 6: [D-Nle$^8$, Nle$^{18}$, Tyr$^{34}$]hPTH(1-34)NH$_2$
Example 7: [D-Nle$^8$]hPTH(1-34)NH$_2$
Example 8: [D-Leu$^8$, Nle$^{18}$, Tyr$^{34}$]hPTH(1-34)NH$_2$
Example 9: [D-Cha$^8$, Nle$^{18}$, Tyr$^{34}$]hPTH(1-34)NH$_2$
Example 10: [D-Phe$^8$, Nle$^{18}$, Tyr$^{34}$]hPTH(1-34)NH$_2$
Example 11: [D-Nal$^8$, Nle$^{18}$, Tyr$^{34}$]hPTH(1-34)NH$_2$
Example 12: [D-Abu$^8$, Nle$^{18}$, Tyr$^{34}$]hPTH(1-34)NH$_2$
Example 13: [D-Met$^8$]hPTH(1-34)NH$_2$
Example 14: [Cha$^{7,11}$, D-Met$^8$]hPTH(1-34)NH$_2$
Example 15: [D-Ile$^8$]hPTH(1-34)NH$_2$
Example 16: [Cha$^{7,11}$, D-Ile$^8$, Nle$^{18}$, Tyr$^{34}$]hPTH(1-34)NH$_2$
Example 17: [D-Ile$^8$, Nle$^{18}$, Tyr$^{34}$]hPTH(1-34)NH$_2$
Example 18: [D-Leu$^8$]hPTH(1-34)NH$_2$
Example 19: [Cha$^{7,11}$, D-Leu$^8$, Nle$^{18}$, Tyr$^{34}$]hPTH(1-34)NH$_2$
Example 20: [D-Val$^8$]hPTH(1-34)NH$_2$
Example 21: [Cha$^{7,11}$, D-Val$^8$, Nle$^{18}$, Tyr$^{34}$]hPTH(1-34)NH$_2$
Example 22: [D-Val$^8$, Nle$^{18}$, Tyr$^{34}$]hPTH(1-34)NH$_2$
Example 23: [D-Cha$^8$]hPTH(1-34)NH$_2$
Example 24: [Cha$^{7,11}$, D-Cha$^8$, Nle$^{18}$, Tyr$^{34}$]hPTH(1-34)NH$_2$
Example 25: [D-Ala$^8$]hPTH(1-34)NH$_2$
Example 26: [Cha$^{7,11}$, D-Ala$^8$, Nle$^{18}$, Tyr$^{34}$]hPTH(1-34)NH$_2$
Example 27: [D-Ala$^8$, Nle$^{18}$, Tyr$^{34}$]hPTH(1-34)NH$_2$
Example 28: [D-Phe$^8$]hPTH(1-34)NH$_2$
Example 29: [Cha$^{7,11}$, D-Phe$^8$, Nle$^{18}$, Tyr$^{34}$]hPTH(1-34)NH$_2$
Example 30: [D-Met$^8$]hPTH(1-34)NH$_2$
Example 31: [D-Nal$^8$]hPTH(1-34)NH$_2$
Example 32: [D-Trp$^8$]hPTH(1-34)NH$_2$
Example 33: [Cha$^{7,11}$, D-Trp$^8$, Nle$^{18}$, Tyr$^{34}$]hPTH(1-34)NH$_2$
Example 34: [D-Trp$^8$, Nle$^{18}$, Tyr$^{34}$]hPTH(1-34)NH$_2$
Example 35: [D-Abu$^8$]hPTH(1-34)NH$_2$
Example 36: [Cha$^{7,11}$, D-Abu$^8$, Nle$^{18}$, Tyr$^{34}$]hPTH(1-34)NH$_2$
Example 37: [des-Met$^8$]hPTH(1-34)NH$_2$ (SEQ ID NO:18)
Example 38: [Cha$^{7,11}$, des-Met$^8$]hPTH(1-34)NH$_2$ (SEQ ID NO:19)
Example 39: [Cha$^{7,11}$, des-Met$^8$, des-Met$^{18}$, Tyr$^{34}$]hPTH(1-34)NH$_2$ (SEQ ID NO:20)
Example 40: [des-Met$^8$, des-Met$^{18}$]hPTH(1-34)NH$_2$ (SEQ ID NO:21)
Example 41: [Cha$^{7,11}$, des-Met$^8$, des-Met$^{18}$]hPTH(1-34)NH$_2$ (SEQ ID NO:22)
Example 42: [des-Met$^8$, Nle$^{18}$, Tyr$^{34}$]hPTH(1-34)NH$_2$ (SEQ ID NO:23)
Example 43: [des-Met$^{18}$]hPTH(1-34)NH$_2$ (SEQ ID NO:24)
Example 44: [Cha$^{7,11}$, des-Met$^{18}$]hPTH(1-34)NH$_2$ (SEQ ID NO:25)
Example 45: [Cha$^{7,11}$, des-Met$^{18}$, Tyr$^{34}$]hPTH(1-34)NH$_2$ (SEQ ID NO:26)
Example 46: [D-Nle$^8$, des-Met$^{18}$, Tyr$^{34}$]hPTH(1-34)NH$_2$
Example 47: [des-Gln$^6$, Nle$^{8,18}$, Tyr$^{34}$]hPTH(1-34)NH$_2$ (SEQ ID NO:27)
Example 48: [des-Leu$^7$, Nle$^{8,18}$, Tyr$^{34}$]hPTH(1-34)NH$_2$ (SEQ ID NO:28)
Example 49: [des-His$^9$, Nle$^{8,18}$, Tyr$^{34}$]hPTH(1-34)NH$_2$ (SEQ ID NO:29)
Example 50: [des-Asn$^{10}$, Nle$^{8,18}$, Tyr$^{34}$]hPTH(1-34)NH$_2$ (SEQ ID NO:30)
Example 51: [des-Leu$^{11}$, Nle$^{8,18}$, Tyr$^{34}$]hPTH(1-34)NH$_2$ (SEQ ID NO:31)
Example 52: [des-Gly$^{12}$, Nle$^{8,18}$, Tyr$^{34}$]hPTH(1-34)NH$_2$ (SEQ ID NO:32)
Example 53: [des-Lys$^{13}$, Nle$^{8,18}$, Tyr$^{34}$]hPTH(1-34)NH$_2$ (SEQ ID NO:33)
Example 54: [des-His$^{14}$, Nle$^{8,18}$, Tyr$^{34}$]hPTH(1-34)NH$_2$ (SEQ ID NO:34)
Example 55: [des-Leu$^{15}$, Nle$^{8,18}$, Tyr$^{34}$]hPTH(1-34)NH$_2$ (SEQ ID NO:35)
Example 56: [des-Asn$^{16}$, Nle$^{8,18}$, Tyr$^{34}$]hPTH(1-34)NH$_2$ (SEQ ID NO:36)
Example 57: [des-Ser$^{17}$, Nle$^{8,18}$, Tyr$^{34}$]hPTH(1-34)NH$_2$ (SEQ ID NO:37)
Example 58: [des-Glu$^{19}$, Nle$^{8,18}$, Tyr$^{34}$]hPTH(1-34)NH$_2$ (SEQ ID NO:38)
Example 59: [des-Arg$^{20}$, Nle$^{8,18}$, Tyr$^{34}$]hPTH(1-34)NH$_2$ (SEQ ID NO:39)
Example 60: [des-Val$^{21}$, Nle$^{8,18}$, Tyr$^{34}$]hPTH(1-34)NH$_2$ (SEQ ID NO:40)
Example 61: [des-Glu$^{22}$, Nle$^{8,18}$, Tyr$^{34}$]hPTH(1-34)NH$_2$ (SEQ ID NO:41)
Example 62: [des-Gln$^6$, Cha$^{7,11}$, Nle$^{8,18}$, Tyr$^{34}$]hPTH(1-34)NH$_2$ (SEQ ID NO:42)
Example 63: [des-Leu$^7$, Nle$^{8,18}$, Cha$^{11}$, Tyr$^{34}$]hPTH(1-34)NH$_2$ (SEQ ID NO:43)
Example 64: [Cha$^{7,11}$, des-His$^9$, Nle$^{8,18}$, Tyr$^{34}$]hPTH(1-34)NH$_2$ (SEQ ID NO:44)
Example 65: [des-Gln$^6$, Cha$^{7,11}$, D-Nle$^8$, Nle$^{18}$, Tyr$^{34}$]hPTH(1-34)NH$_2$ Example 66: [des-Leu$^7$, D-Nle$^8$, Cha$^{11}$, Nle$^{18}$, Tyr$^{34}$]hPTH(1-34)NH$_2$
Example 67: [Cha$^{7,11}$, D-Nle$^8$, des-His$^9$, Nle$^{18}$, Tyr$^{34}$]hPTH(1-34)NH$_2$
Example 68: [Cha$^{7,11}$, des-Met$^8$, des-His$^9$, des-Asn$^{10}$]hPTH(1-34)NH$_2$ (SEQ ID NO:45)
Example 69: [Cha$^{7,11}$, des-Ser$^{17}$, des-Met$^{18}$, des-Glu$^{19}$]hPTH(1-34)NH$_2$ (SEQ ID NO:46)
Example 70: [D-Met$^8$, Nle$^{18}$, Tyr$^{34}$]hPTH(1-34)NH$_2$
Example 71: [D-Met$^8$, Tyr$^{34}$]hPTH(1-34)NH$_2$
Example 72: [D-Nle$^8$, Nle$^{18}$, Tyr$^{34}$]hPTH(7-34)NH$_2$
Example 73: [D-Nle$^8$, Nle$^{18}$]hPTH(7-34)NH$_2$
Example 74: [Ile$^5$, D-Leu$^8$]hPTHrP(1-34)NH$_2$
Example 75: [Ile$^5$, D-Leu$^8$, Trp$^{23}$]hPTHrP(1-34)NH$_2$
Example 76: [Ile$^5$, des-Leu$^8$, Trp$^{23}$]hPTHrP(1-34)NH$_2$ (SEQ ID NO:47)
Example 77: [Ile$^5$, des-Leu$^8$]hPTHrP(1-34)NH$_2$ (SEQ ID NO:48)
Example 78: [des-Leu$^8$, Trp$^{23}$]hPTHrP(1-34)NH$_2$ (SEQ ID NO:49)
Example 79: [Ile$^5$, des-Leu$^{18}$]hPTHrP(1-34)NH$_2$ (SEQ ID NO:50)
Example 80: [Ile$^5$, des-Leu$^{18}$, Trp$^{23}$]hPTHrP(1-34)NH$_2$ (SEQ ID NO:51)
Example 81: [des-Leu$^{18}$, Trp$^{23}$]hPTHrP(1-34)NH$_2$ (SEQ ID NO:52)
Example 82: [Ile$^5$, D-Leu$^8$, Glu$^{22,25}$, Leu$^{23,28,31}$, Lys$^{26,30}$, Aib$^{29}$]hPTHrP(1-34)NH$_2$
Example 83: [Ile$^5$, D-Leu$^8$, Glu$^{22,25}$, Trp$^{23}$, Lys$^{26,30}$, Leu$^{28,31}$, Aib$^{29}$]hPTHrP(1-34)NH$_2$
Example 84: [Ile$^5$, D-Leu$^8$, Glu$^{22,25,29}$, Leu$^{23,28,31}$, Lys$^{26,30}$]hPTHrP(1-34)NH$_2$
Example 85: [Ile$^5$, D-Leu$^8$, Glu$^{22,25,29}$, Trp$^{23}$, Lys$^{26,30}$, Leu$^{28,31}$]hPTHrP(1-34)NH$_2$
Example 86: [D-Leu$^8$, Trp$^{23}$]hPTHrP(7-34)NH$_2$

What is claimed is:

1. A human PTH analogue of the formula, [Cha$^{7,11}$, des-Met$^8$, Nle$^{18}$, Tyr$^{34}$]hPTH(1-34)NH$_2$ (SEQ ID NO:16), which selectively binds to the PTH2 receptor, or a pharmaceutically acceptable salt thereof.

2. A human PTH analogue which selectively binds to the PTH2 receptor, wherein said analogue is selected from the group consisting of

[Cha$^{7,11}$, des-Met$^8$, Nle$^{18}$, Tyr$^{34}$]hPTH(1-34)NH$_2$ (SEQ ID NO:16),

[Cha$^{7,11}$, D-Nle$^8$, des-Met$^{18}$, Tyr$^{34}$]hPTH(1-34)NH$_2$, and

[Cha$^{7,11}$, D-Nle$^8$, Nle$^{18}$, Tyr$^{34}$]hPTH(1-34)NH$_2$, which selectively binds to the PTH2 receptor, or a pharmaceutically acceptable salt thereof.

3. A pharmaceutical composition comprising an analogue according to claim 2 or a pharmaceutically acceptable salt thereof and a pharmaceutically acceptable carrier.

* * * * *